United States Patent
Kofod-Hansen et al.

(10) Patent No.: US 8,859,731 B2
(45) Date of Patent: Oct. 14, 2014

(54) SELECTIVE MODIFICATION OF PROTEINS

(75) Inventors: Mikael Kofod-Hansen, Koebenhavn (DK); Henning Ralf Stennicke, Kokkedal (DK); Soeren Oestergaard, Broenshoej (DK); Henrik Oestergaard, Oelstykke (DK)

(73) Assignee: Novo Nordisk A/S, Bagsvaerd (DK)

( * ) Notice: Subject to any disclaimer, the term of this patent is extended or adjusted under 35 U.S.C. 154(b) by 102 days.

(21) Appl. No.: 13/638,802

(22) PCT Filed: Apr. 12, 2011

(86) PCT No.: PCT/EP2011/055686
§ 371 (c)(1),
(2), (4) Date: Nov. 20, 2012

(87) PCT Pub. No.: WO2011/131510
PCT Pub. Date: Oct. 27, 2011

(65) Prior Publication Data
US 2013/0071383 A1    Mar. 21, 2013

Related U.S. Application Data

(60) Provisional application No. 61/327,949, filed on Apr. 26, 2010.

(30) Foreign Application Priority Data

Apr. 21, 2010  (EP) .................................... 10160563

(51) Int. Cl.
*A61K 38/37*  (2006.01)
*A61K 38/36*  (2006.01)
*C07K 14/745*  (2006.01)
*C07K 14/755*  (2006.01)
*A61K 47/48*  (2006.01)
*B82Y 5/00*  (2011.01)
*C07K 1/107*  (2006.01)
*A61K 38/00*  (2006.01)

(52) U.S. Cl.
CPC ......... *C07K 14/755* (2013.01); *A61K 47/48338* (2013.01); *B82Y 5/00* (2013.01); *A61K 47/48346* (2013.01); *A61K 47/48215* (2013.01); *C07K 1/1077* (2013.01); *A61K 47/48084* (2013.01); *A61K 47/48284* (2013.01); *A61K 38/00* (2013.01)
USPC ........... 530/333; 530/380; 530/381; 530/383; 514/13.7; 514/13.5; 514/14.1; 514/1.1

(58) Field of Classification Search
CPC ....... A61K 38/37; A61K 38/36; A61K 38/10; A61K 38/04; A61K 38/00; A61K 47/48338; A61K 47/48246; A61K 47/48346; A61K 47/48; A61K 47/48023; A61K 47/48007; C07K 14/755; C07K 14/745; C07K 14/001; C07K 14/00
See application file for complete search history.

(56) References Cited

U.S. PATENT DOCUMENTS

2004/0001838 A1 *  1/2004  Zhao et al. ................. 424/178.1

FOREIGN PATENT DOCUMENTS

WO  2008/003707 A2  1/2008
WO  2009/027369 A1  3/2009

OTHER PUBLICATIONS

Pilch et al., PNAS (2006) 103(8), 2800-2804.*
Lucke et al., European Journal of Pharmaceutics and Biopharmaceutics (2003) 55, 27-33.*
Hermanson, Bioconjugate Techniques, 2nd ed. Rockford, IL: Academic Press, 2008.*
Dawson et al., Journal of Thrombosis and Thrombolysis., "Manipulation of Thrombin Exosite I, by Ligand-Directed Covalent Modification", 2007, vol. 5, No. 10, pp. 2062-2069.

* cited by examiner

Primary Examiner — Karlheinz R Skowronek
Assistant Examiner — Catherine Mader
(74) Attorney, Agent, or Firm — Nonna G. Akopyan; Reza Green; Richard W. Bork

(57) ABSTRACT

A method of selectively introducing a substituent into a protein proximal to a binding site on the protein for a homing peptide, comprising: (a) contacting the protein with a compound comprising a homing peptide having the ability to bind to the binding site of the protein; and (b) allowing a moiety on the protein proximal to the binding site to react with the compound comprising the homing peptide, thereby to transfer the substituent G onto the protein.

12 Claims, 3 Drawing Sheets

SELECTIVE MODIFICATION OF PROTEINS

CROSS-REFERENCE TO RELATED APPLICATIONS

This application is a 35 U.S.C. §371 national stage application of international Patent Application PCT/EP2011/055686 (published as WO 2011/131510), filed Apr. 12, 2011, which claimed priority of European Patent Application 10160563.2, filed Apr. 21, 2010; this application further claims priority under 35 U.S.C. §119 of U.S. Provisional Application 61/327,949, filed Apr. 26, 2010.

FIELD OF THE INVENTION

The present invention relates to methods for selectively introducing substituents into proteins, targeted reagents and their use in said methods, and proteins which are obtainable from said methods.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Sep. 24, 2012. The Sequence Listing is made up of 43 kilobytes, and the information contained in the attached "SEQUENCE LISTING" is identical to the information in the specification as originally filed. No new matter is added.

BACKGROUND OF THE INVENTION

Selective modification of proteins for pharmaceutical purposes is an increasingly important field. By selectively modifying proteins, for example by the addition of polyethyleneglycol (PEG), the pharmacological profile and half-life of proteins can be modified. In particular, it is desirable to generate long acting variants of proteins for use as pharmaceuticals. A number of techniques have been developed to selectively modify particular regions of proteins. Selective modification is particularly difficult for large proteins such as Factor VIII and Von Willebrand factor (vWF).

Proteins may be modified by reacting them with unselective reagents, which are capable of forming bonds to residues on the protein. A large range of different products will be formed by such methods, because the reagent can react with any suitable residue on the protein. An extension of this technique involves blocking specific sites on a protein with ligands that bind to these sites. The ligand/protein conjugate is then added to an unselective reagent that reacts with the unblocked sites on the protein, leaving the blocked sites unmodified.

Selective modification of proteins has also been investigated. One technique for selectively modifying proteins involves introducing cysteine residues as mutations at pre-defined sites in the protein. The mutated protein can then be reacted with a reagent that selectively reacts with the cysteine residues to give a selectively modified protein. Another technique involves adding a large substituent, typically PEG, directly to a protein by reacting the protein with a complex comprising the large substituent and a ligand that binds selectively to the protein.

Dawson et al, *Journal of Thrombosis and Haemostasis*, 5, 2062 to 2069 describes techniques for introducing labels into thrombin using targeting ligands and photocrosslinking reactions.

There is thus a need for more efficient and selective techniques for modifying proteins, particularly large proteins.

SUMMARY OF THE INVENTION

The present inventors have devised a new method of selectively introducing a substituent into Factor VIII proximal to a binding site on Factor VIII for a homing peptide. This method has general applicability, and can be used to selectively introduce substituents into any protein, but is particularly useful for large proteins. One application of the methods of the present invention is to provide modified proteins that have an increased plasma half-life. Such long acting modified proteins are potentially useful as pharmaceuticals, since the increased plasma half-life may allow reduced dosages and/or reduced dosing frequency.

Thus, the present invention provides a method of selectively introducing a substituent (G) into a protein proximal to a binding site on the protein for a homing peptide (P), comprising:

(a) contacting the protein with a compound of formula (I) ("targeted reagent") so that the targeted reagent binds to the protein:

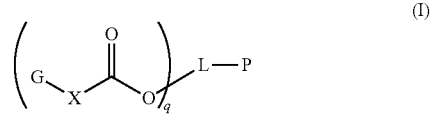

(I)

wherein:
P is a homing peptide comprising 5-20, or 5-19, or 5-18, or 5-17, or 5-16, or 5-15 amino acids,
L is a linker,
X is a direct bond or NH,
G is a substituent capable of subsequent modification ($G_1$) or a substituent that is capable of increasing the plasma half-life of the target protein ($G_2$), and
q is an integer of from 1 to 9 wherein each G is the same or different if q is greater than 1; and (b) allowing a moiety on the protein proximal to the binding site to react with the targeted reagent, thereby to transfer the substituent G onto the protein via transfer of an acyl group from an ester group present in the targeted reagent to the protein.

The present invention further provides:
a method wherein the homing peptide does not contain any lysine residues that carries an unsubstituted epsilon-amino group;
a method wherein the target protein comprises at least one surface exposed lysine;
a method wherein the target protein that comprises at least one surface exposed lysine close to the binding site of the homing peptide (such as e.g. within a distance of about 100 Å, 50 Å, or 25 Å);
a method wherein the targeted reagent is prepared synthetically (either fully synthetically or semi-synthetically);
a method wherein the total mass of the targeted reagent does not exceed 3000 Da, 2500 Da, 2000 Da, 1500 Da, 1000 Da, or 500 Da.
a protein which is substituted proximal to a binding site for a homing peptide on the protein and which is obtainable by the method defined above;
a targeted reagent of formula (I) as defined above;
use of a targeted reagent of formula (I) as defined above to selectively modify a protein as defined above; and a pharmaceutical composition comprising a protein as defined above and a pharmaceutically acceptable diluent or carrier.

DESCRIPTION OF THE SEQUENCES MENTIONED HEREIN

Figure 1:
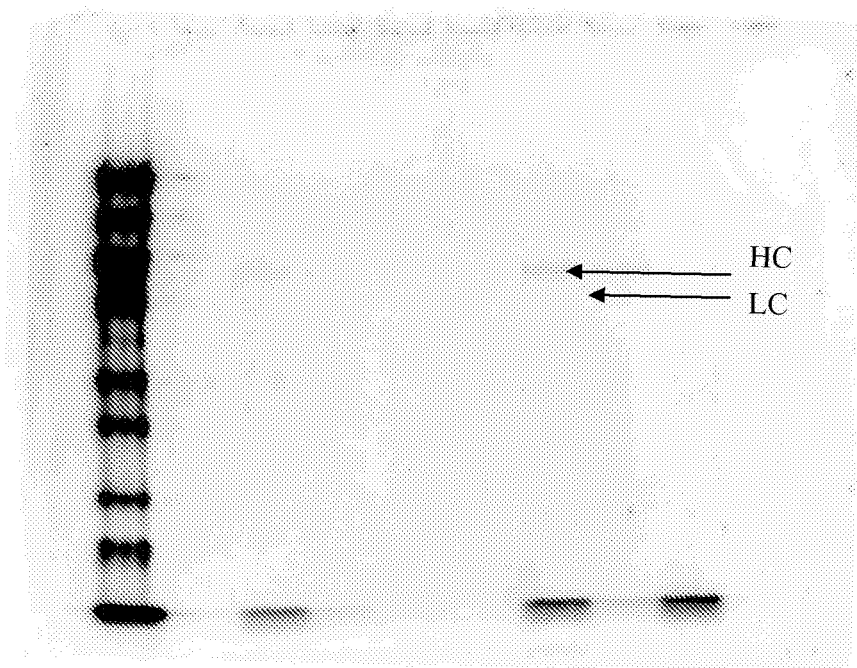
FIG. 1 is a Western blot obtained for the product formed from the reaction of Compound 22 with B domain deleted Factor VIII. Lanes: 1: Biotinylated marker cell signaling technologies, 2 microliter and seeblue 2 marker, 3 microliter; 2: BDD-FVIII (50 ng); 3-6: BDD-FVIII (50 ng protein pr. lane) incubated with solutions of compounds 22 in decreasing amounts (decrements of factor 10), 7-10: BDD-FVIII (100 ng protein pr. lane) incubated with solutions of compounds 22 in decreasing amounts (decrements of factor 10). "HC" refers to "heavy chain" and "LC" refers to "light chain". The Western blot demonstrates that biotin was introduced into the heavy chain of Factor VIII.

SEQ ID NO 1 to 44 provide the polypeptide sequences of the invention. SEQ ID NO 42 is present in the targeted reagents of Compounds 1, 2, 4, 5, 9, 10, 18 to 20. SEQ ID NO 40 is present in Compounds 7, 8 and 17.

DETAILED DESCRIPTION OF THE INVENTION

General Definitions

It is to be understood that different applications of the disclosed methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a protein" includes "proteins", reference to "a homing peptide" includes two or more such homing peptides, and the like.

All publications, patents and patent applications cited herein, whether supra or infra, are hereby incorporated by reference in their entirety.

As used herein, unless otherwise specified, a $C_1$ to $C_6$ alkyl moiety is a linear or branched alkyl moiety containing from 1 to 6 carbon atoms, such as a $C_1$ to $C_4$ alkyl moiety. Examples of $C_1$ to $C_6$ alkyl moieties include methyl, ethyl, n-propyl, i-propyl, n-butyl and t-butyl moieties. For the avoidance of doubt, where two alkyl moieties are present in a substituent, the alkyl moieties may be the same or different.

As used herein, unless otherwise specified, an alkylene group is any divalent linear or branched alkylene group, and is preferably a $C_1$ to $C_{10}$ alkylene group, more preferably a $C_1$ to $C_4$ alkylene group. Preferred linear $C_1$ to $C_4$ alkylene groups are methylene, ethylene, n-propylene and n-butylene groups. Methylene and n-propylene groups are preferred. Branched $C_2$ to $C_4$ alkylene groups include —CH(CH$_3$)—, —CH(CH$_3$)—CH$_2$— and —CH$_2$—CH(CH$_3$)—.

As used herein, unless otherwise specified, a $C_1$ to $C_6$ alkoxy group is typically a $C_1$ to $C_6$ alkyl group attached to an oxygen atom, said $C_1$ to $C_6$ alkyl group being linear or branched. Preferred alkoxy groups include methoxy, ethoxy, n-propoxy, i-propoxy, n-butoxy, sec-butoxy and t-butoxy.

As used herein, a halogen is chlorine, fluorine, bromine or iodine. A halogen is typically fluorine, chlorine or bromine and preferably fluorine or chlorine.

As used herein, a $C_6$ to $C_{10}$ aryl group is preferably a phenyl or naphthyl group. More preferably, it is a phenyl group.

As used herein, a $C_6$ to $C_{10}$ arylene group is a diradical of $C_6$ to $C_{10}$ aryl group, and is preferably a phenylene group.

As used herein, unless otherwise specified, a $C_3$ to $C_8$ cycloalkyl group is monocyclic cycloalkyl group containing from 3 to 8 carbon atoms, such as a $C_3$ to $C_6$ cycloalkyl group. Preferred $C_3$ to $C_6$ cycloalkyl groups include cyclopropyl, cyclobutyl, cyclopentyl and cyclohexyl.

As used herein, a $C_3$ to $C_8$ cycloalkylene group is diradical of a $C_3$ to $C_8$ cycloalkyl group, preferably a diradical of a $C_3$ to $C_6$ cycloalkyl group.

Targeting Method

The present invention relates to a method for selectively introducing a substituent into a protein at a suitable site. In particular, the method comprises contacting a protein with a targeted reagent. The targeted reagent comprises a homing peptide (P), a linker moiety (L) and one or more substituents (G). The bond between the homing peptide (P) and the linker (L) is typically an amide bond. The or each substituent (G) is attached to the linker via an ester or carbamate bond, as shown below:

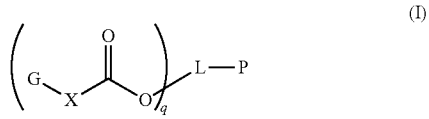

(I)

X preferably represents a direct bond, so that the targeted reagent is a compound of formula (I'):

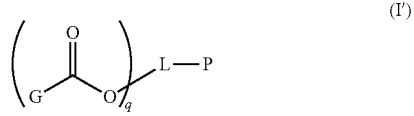

(I')

When the targeted reagent comes into contact with the target protein, the homing peptide (P) binds to a specific site on the target protein. While the targeted reagent is bound to the protein, a reactive moiety on the protein proximal to the binding site of the homing peptide (P) on the protein is allowed to react with the carbonyl carbon of the ester or carbamate connecting the substituent (G) to the linker (L). Thus, interactions between the homing peptide and the protein dictate which region of the target protein the substituent (G) is introduced into.

A reactive moiety on the protein is typically on the side chain of an amino acid in the protein. A nucleophilic side chain, such as a side chain comprising an alcohol or amine, is preferred. Thus, step (b) of the method of the invention preferably involves allowing an alcohol group on a side chain of a serine, threonine or tyrosine amino acid residue proximal to the binding site to react with the targeted reagent. Alternatively, step (b) of the method of the invention preferably involves allowing an amine group on a side chain of a lysine amino acid residue proximal to the binding site to react with the targeted reagent. It is typically not necessary to provide any external energy for this reaction to occur at a sufficient rate.

The reaction between the said reactive moiety on the target protein and the carbonyl carbon of the ester or carbamate connecting the substituent (G) to the linker (L) breaks the ester or carbamate bond, so that (i) a new covalent bond is formed between the target protein and carbonyl carbon attached to the substituent (G), and (ii) the linker/homing peptide portion —O-L-P of the starting targeted reagent is released.

In this way, a substituent (G) is selectively introduced into the target protein proximal to a binding site on the target protein of a homing peptide.

Target Protein

The techniques and methods of the present invention are suitable for selectively introducing substituents into any protein. However, the present invention is particularly applicable to large proteins. Thus the protein typically has a mass of 50 to 3000 kDa, preferably 100 to 3000 kDa, more preferably 150 to 3000 kDa.

Preferred proteins include Factor VII, Factor VIIa, Factor VIII and Von Willebrand Factor (vWF), tissue factor (TF), cytokines, growth hormones, antibodies and antibody fragments such as e.g. antigen binding fragments. Active fragments of the above proteins are also preferred, for example active fragments of Von Willebrand Factor. Factor VIII, Factor VII and vWF are more preferred target proteins, with Factor VIII most preferred.

Factor VII is a plasma glycoprotein that circulates in blood as a single chain zymogen. The zymogen is catalytically inactive. Single-chain factor VII may be converted to two-chain factor VIIa by factor Xa.

The mature Factor VIII molecule consists of 2332 amino acids which can be grouped into three major, homologous A domains, two homologous C domains, a B Domain, and three minor (peptide) domains which are arranged in the order: A1-a1-A2-a2-B-a3-A3-C1-C2. During its secretion into plasma Factor VIII is processed intracellularly into a series of metal-ion linked heterodimers as single chain Factor VIII is cleaved at the B-a3 boundary. This processing leads to a heavy chain (HC) consisting mainly of the A1, the A2 and the B-domain which has a molecular size of approx. 200 kDa. The heavy chain is bound via a metal ion to the light chain, which consists mainly of the A3, the C1 and the C2 domain. In plasma, this heterodimeric Factor VIII binds with high affinity to von Willebrand Factor (VWF), which protects it from premature catabolism. The half-life of non-activated Factor VIII bound to vWF is about 12 hours in plasma. The light chain (LC) consists of domains a3-A3-C1-C2. When activated by thrombin, the a3 domain is lost to give A3-C1-C2 (LC').

During the blood coagulation process, Factor VIII is activated via proteolytic cleavage by Factor Xa and thrombin at amino acids Arg372 and Arg740 within the heavy chain and at Arg1689 in the light chain (LC) resulting in the release of von Willebrand Factor and generating the activated Factor VIII heterotrimer which will form the tenase complex on phospholipid surfaces with Factor IXa and Factor X provided that $Ca^{2+}$ is present. The heterotrimer consists of the A1 domain, a 50 kDa fragment, the A2 domain a 43 kDa fragment and the light chain (A3-C1-C2), a 73 kDa fragment. Thus the active form of Factor VIII (Factor VIIIa) consists of an A1-subunit associated through the divalent metal ion linkage to a thrombin-cleaved A3-C1-C2 light chain and a free A2 subunit relatively loosely associated with the A1 and the A3 domain.

A Factor VIII molecule consisting of the heavy chain (HC) and light chain (LC) of Factor VIII connected with a small linker derived from the B-domain (B-domain deleted Factor VIII or BDD-FVIII) retains the biological activity of full length (native) Factor VIII.

As used herein, the term "Factor VIII" includes any Factor VIII that is therapeutically useful, e.g. effective in preventing or treating bleeding. This includes, without limitation, wild-type human Factor VIII, hybrid human/porcine Factor VIII and B-domain deleted human Factor VIII.

The term "Factor VIII" is intended to encompass, without limitation, polypeptides having the amino acid sequence as described in Toole et al., Nature 1984, 312: 342-347 (wild-type human Factor VIII), as well as wild-type Factor VIII derived from other species, such as, e.g., bovine, porcine, canine, murine, and salmon Factor VIII. It further encompasses natural allelic variations of Factor VIII that may exist and occur from one individual to another. Also, degree and location of glycosylation or other post-translation modifications may vary depending on the chosen host cells and the nature of the host cellular environment. The term "Factor VIII" is also intended to encompass uncleaved (zymogen) forms, as well as those that have been proteolytically processed to yield their respective bioactive forms, which may be designated Factor VIIIa.

The term "Factor VIII" is intended to encompass polypeptides with a slightly modified amino acid sequence, for instance, polypeptides having a modified N-terminal end including N-terminal amino acid deletions or additions, and/or polypeptides that have been chemically modified relative to human Factor VIII. The term "Factor VIII" is intended to include variants of Factor VIII, whether exhibiting substantially the same or better bioactivity than wild-type Factor VIII, or, alternatively, exhibiting substantially modified or reduced bioactivity relative to wild-type Factor VIII, include, without limitation, polypeptides having an amino acid sequence that differs from the sequence of wild-type Factor VIII by insertion, deletion, or substitution of one or more amino acids.

Non-limiting examples of Factor VIII include plasma-derived human Factor VIII as described, e.g., in Fulcher et al.; Proc. Acad. Nat. Sci. USA 1982; 79:1648-1652, and Rotblat et al.; Biochemistry 1985; 24:4294-4300, and plasma-derived porcine FVIII as described, e.g., in Fass et al.; Blood 1982; 59: 594-600 and Knutson et al.; Blood 1982; 59: 615-624. Non-limiting examples of Factor VIII sequence variants are described, e.g., in Lollar et al.; Blood 2000; 95(2): 564-568 (hybrid porcine/human FVIII polypeptides) and Lollar et al.; Blood 2001; 97(1): 169-174.

The cloning of the cDNA for Factor VIII (Wood, W. I., et al. (1984) Nature 312, 330-336; Vehar, G. A., et al. (1984) Nature 312, 337-342) made it possible to express Factor VIII recombinantly leading to the development of several recombinant Factor VIII products, which were approved by the regulatory authorities between 1992 and 2003. The fact that the central B domain of the Factor VIII polypeptide chain residing between amino acids Arg-740 and Glu-1649 does not seem to be necessary for full biological activity has also led to the development of a B-domain deleted Factor VIII. See also Kjalke M, Heding A, Talbo G, Persson E, Thomsen J and Ezban M (1995), "Amino acid residues 721-729 are required for full Factor VIII activity". Eur. J. Biochem: 234: 773-779. Factor VIII as used herein includes all variants of Factor VIII, including those in which one or more domains or regions have been deleted.

In the present invention, the substituent (G) is typically introduced into the heavy chain of Factor VIII, preferably into the A1, A2 or B domain of the heavy chain, for example into the A2 domain of the heavy chain.

Von Willebrand Factor (vWF) is a glycoprotein present in blood plasma. The basic vWF monomer is a 2050 amino acid protein, comprising a number of domains including a D'/D3 domain, which binds to Factor VIII.

Tissue Factor is also known as thromboplastin or Factor III.

The cytokine is typically selected from Interleukin-1 (IL-1), Interleukin-2 (IL-2), Interleukin-6 (IL-6) Interleukin-8 (IL-8), Interleukin-21 (IL-21), Interleukin-32 (IL-32), Interleukin-35 (IL-35), Tumor Necrosis Factor-α (TNF-α), Tumor Necrosis Factor-β (TNF-β), Interferon-γ (INF-γ) and a Colony Stimulating Factor (CSF).

The antibody can be a human antibody or a chimeric antibody. It is preferably a monoclonal antibody. Preferably the antibody is an IgG1 (e.g. IgG1, κ), IgG3 (e.g. IgG3, κ) and IgG4 (e.g. IgG4, κ) antibody. However, other antibody isotypes are also encompassed by the invention, including IgG2, IgM, IgA1, IgA2, secretory IgA, IgD, and IgE. Suitable antigen-binding fragments of such antibodies include Fab, F(ab')$_2$, Fv, single chain Fv fragments or bispecific antibodies. Furthermore, the antigen-binding fragments include binding-domain immunoglobulin fusion proteins comprising (i) a binding domain polypeptide (such as a heavy chain variable region or a light chain variable region) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. Such binding-domain immunoglobulin fusion proteins are further disclosed in US 2003/0118592 and US 2003/0133939.

Homing Peptide

As used herein, the term "homing peptide" refers to a peptide that is capable of binding to the protein that is to be modified. The homing peptide is preferably a synthetic peptide. Thus, a homing peptide is an affinity ligand. Alternatively, the homing peptide could be described as a targeting ligand. The binding of a homing peptide to a protein can easily be determined by techniques known to one skilled in the art. A homing peptide of the invention typically binds to the target protein with greater affinity than it binds to another protein for which it is not a homing peptide. Typically, the binding affinity ($K_d$) of the homing peptide for the target protein is less than 1000 nM, preferably less than 100 nM and more preferably less than 10 nM.

Suitable homing peptides may be derived from any source, such as a library, particularly a combinatorial library. Preferred combinatorial libraries include bead libraries, aptamer libraries, phage display libraries and rationally designed libraries. The homing peptides may be rationally designed peptides or peptides that are already known to bind to a certain protein. For example, the homing peptide may be built in situ using Sunesis technology, as described in WO 2000/00823, WO 2002/42773, WO 2003/046200, WO 2003/046200 and WO 2003/087054, when a specific modification site is desired. Alternatively mimetics or fragments of peptides that are known to bind to the protein of interest may be screened. For example, heparin mimetics and fragments are potential homing peptides for proteins that heparin is known to bind to. In an alternative example, fragments of vWF are potential homing peptides for Factor VIII. Rational designed of homing peptides includes, for example, the use of positively charged homing peptides to target negatively charged domains in the target protein.

Once potential homing peptides have been prepared, for example in the form of a library, standard techniques can be used to determine which peptides bind to the target protein.

Typically, a peptide display technique is used to identify homing peptides. Generally in such a technique, solid phase bead libraries are incubated with a labeled version of the protein of interest. After incubation, the bead libraries are washed and then incubated with a reagent that binds to the labeled protein. For example, a biotinylated protein is typically incubated with a streptavidin reagent. The beads that carry the most labeled protein are separated from the library and homing peptides sequenced.

Alternatively, a phage display technique may be conducted using either commercially available or custom libraries based on random sequences or sequences derived from known interacting proteins or ligands using methods known to those skilled in the art. The elution of binding phages is typically conducted either by a pH change or as a competitive elution with the target protein itself or with the ligand to which the binding should be disrupted. High throughput screening of a combinatorial library is a preferred technique.

Once a homing peptide has been identified, it can be desirable to map the site on the protein where binding between the homing peptide and the protein occurs. To achieve this, the homing peptide is coupled to a conjugating group such as Sulfo-SBED (Pierce) or to a biotinylated conjugating group, to provide a probe. This probe is then used to map the binding site of the homing peptide on the protein surface by one or more of the following methods: digestion (for example by trypsin or thrombin), affinity absorption, LC-MS (liquid chromatography-mass spectrometry), MS (mass spectrometry) or HX-MS (hydrogen exchange mass spectrometry). Based on this mapping technique, any homing peptides that bind to regions of the protein that are of known biological importance can be eliminated.

The homing peptide typically contains from 5 to 50 amino acids, preferably from 5-20, 5-19, 5-18, 5-17, 5-16, 5-15, 5-12, 5-10, 6-15, 6-12, 6-10, 7-15, and most preferably from 7 to 13 amino acids.

The end of the homing peptide that is not connected to the linker (L) preferably terminates with a carboxyl group (C-terminus), an amino group (N-terminus), or any variant or derivative thereof. The C-terminus or N-terminus is typically protected (i.e. as a variant or derivative), to prevent unwanted reactions (both during synthesis of the targeted reagent and during subsequent reactions involving the targeted reagent). For example, the C-terminus is preferably protected as an amide, such as $—CO_2NH_2$.

A number of peptide sequences that bind Factor VIII have been identified. These are listed as SEQ ID NO 1 to 44. Thus, in a preferred embodiment of the invention, the homing peptide is a peptide of length 5 to 50 amino acids comprising any one of SEQ ID NO 1 to 44:

| | |
|---|---|
| 1. | RQ7HVYRQ |
| 2. | 1R2HGGYQ4RV |
| 3. | RHYRCHFQGR |
| 4. | 1H2RWQQQLDR |
| 5. | VQ2RQ3VQYHR |
| 6. | VR6VRQLRR73SH |
| 7. | VR4Q2QRLQS |
| 8. | VRLR7QQR7QH |
| 9. | RR4GQ68VFH |

-continued

| | |
|---|---|
| 10. | HR4SQV2R5DR |
| 11. | 1RFRQS7RVYQV |
| 12. | RQ48G5R2HQ |
| 13. | 8R2V5RDYQQ |
| 14. | VV6VRH6HR5RQ |
| 15. | RQYVV86RR6RQ |
| 16. | RR6VR78RV2VH |
| 17. | 1R6V56R8 |
| 18. | HQ7R6VSYRR |
| 19. | 186V6Q8R6HR |
| 20. | R66V5HR |
| 21. | RS6VGR68Q |
| 22. | HR5L68R |
| 23. | 1RLHHR4VRV68V |
| 24. | DRLPHR6SV868R |
| 25. | RGYVH68R21H |
| 26. | RR4GQ68VFH |
| 27. | R1686VYRH |
| 28. | DH68HYRRG5QV |
| 29. | 1HYRQVRPL8G |
| 30. | VHYGRPLRQ2V8 |
| 31. | 1V2HPYRPLR1 |
| 32. | 1Q2RPYSSH7HH |
| 33. | RQYRPH6VWHH |
| 34. | 1P3RRF7HH |
| 35. | RRWQRHWV6V1 |
| 36. | R8YLRRLHR |
| 37. | HR5SFR2VH |
| 38. | QR5HV6RVS6G1 |
| 39. | 1R2 PRF8RVFPG |
| 40. | 1RFGPRFQ2VS |
| 41. | RR6QYD8R2RR |
| 42. | R86L5RH |
| 43. | SYEWSQYE |
| 44. | SV2QFRPGFR1 | wherein
1=Aib (2-aminoisobutyric acid)
2=L-Nal2 (L-2-Naphthylalanine)
3=L-Tic (L-1,2,3,4-tetrahydroisoquinoline-3-carboxylic acid)
4=L-Sty (Styrylalanine)
5=L-Bip (L-Biphenylalanine)
6=Pya3 (L-3-pyridylalanine)
7=L-Dip (L-Diphenylalanine)
8=L-Hph (L-homophenylalanine)

Alternatively, in another embodiment of the invention, the homing peptide that binds Factor VIII comprises one of the sequences described in: Knor et al, *Journal of Thrombosis and Haemostasis,* 6: 470-477; Jungbauer et al, *J. Peptide Res,* 2002, 59, 174-182; Jungbauer et al, *Journal of Chromatography B,* 715 (1998) 191-201; and CA 2301959 A. In particular, the homing peptide for Factor VIII typically comprises one of the following sequences SEQ ID NO 45-139 (the cysteine residue can optionally be omitted or replaced):

| | | | | |
|---|---|---|---|---|
| GCVSGCLC (45) | CVSGCLCP (64) | VSGCLCPP (83) | SGCLCPPG (102) | GCLCPPCM (121) |
| CLCPPGMV (46) | LCDPGMVR (65) | CPPGMVRH (84) | PPGMVRHE (103) | PGMVRHEN (122) |
| GMVRHENR (47) | MVRHENRC (66) | VRHENRCV (85) | RHENRCVA (104) | HENRCVAL (123) |
| ENRCVALE (48) | NRCVALER (67) | RCVALERC (86) | CVALERCP (105) | VALERCPC (124) |
| ALERCPCF (49) | LERCPCFH (68) | ERCPCFHQ (87) | RCPCFHQG (106) | CPCFHQGK (125) |
| PCFHQGKE (50) | CFHQGKEY (69) | FHQGKEYA (88) | HQGKEYAP (107 | QGKEYAPG (126) |
| GKEYAPGE (51) | LEYAPGET (70) | EYAPGETV (89) | YAPGETVK (108) | ARGETVKI (127) |
| PGETVKIG (52) | GETVKIGC (71) | QTVKIGCN (90) | TVKIGCNT (109) | VKIGCNTC (128) |
| KIGCNTCV (53) | IGCNTCVC (72) | GCNTCVCR (91) | CNTCVCRD (110) | NTCVCRDR (129) |
| TCVCRDRK (54) | CVCRDRKW (73) | VCRDRKWN (92) | CRDRKWNC (111) | RDRKWNCT (130) |
| DRKWNCTD (55) | RKWNCTDH (74) | KWNCTDHV (93) | WNCTDHVC (112) | VMIKCEYC (131) |
| VMIKCEEF (56) | VMIKEFYC (75) | VMIKEFEF (94) | VMIKWEYC (113) | VMIKWEEF (132) |
| VMKSCEYC (57) | VMKSCEEF (76) | VMKSEFYC (95) | VMKSEFEF (114) | VMKSWEYC (133) |
| VMKSWEEF (58) | EWIKCEYC (77) | EWIKCEEF (96) | EWIKEFYC (115) | EWIKEFEF (134) |
| EWIKWEYC (59) | EWIKWEEF (78) | EWKSCEYC (97) | EWKSCEEF (116) | EWKSEFYC (135) |
| EWKSEFEF (60) | EWKSWEYC (79) | EWKSWEEF (98) | EYIKCEYC (117) | EYIKCEEF (136) |
| EYIKEFYC (61) | EYIKEFEF (80) | EYIKWEYC (99) | EYIKWEEF (118) | EYKCEYC (137) |
| EYKSCEEF (62) | EYKSEFYC (81) | EYKSEFEF (100) | EYKSWEYC (119) | EYKSWEEF (138) |
| LCPPGMVRHE (63) | RCPCFHQGK (82) | CFHQGKEYA (101) | RDRKQNCTDHVC (120) | EYHSWEYC (139) |

The present invention also relates to the use of the above sequences to target a substituent G to Factor VIII, whereby the substituent is transferred to Factor VIII.

If the target protein is Factor VII, the homing peptides typically comprises one of the following sequences (a) ALCDDPRVDRWYCQFVEG (SEQ ID NO 140) and EEWEVLCWTWETCER (SEQ ID NO 141) described in Roberge et al., *Biochem J.,* 2002, 363, 387-393, (b) EAALCDDPRLDRWYCIFAGE (SEQ ID NO 142) described in Dennis et al., *Nature* 2000, 404, 465-470, (c) EWEVLCWTWETCERGE, (SEQ ID NO 143) EEWEVLCWTWETCERGEG (SEQ ID NO 144), MEEWEVLCWTWETCERGEGQ (SEQ ID NO 145), EVLCWTWETCER (SEQ ID NO 146), VLCWTWETCER (SEQ ID NO 146), LCWTWETCER (SEQ ID NO 147), CWTWETCERGEGQ (SEQ ID NO 148), WEVLCWTWETCE (SEQ ID NO 149) and WEVLCWTWETC (SEQ ID NO 150) described in Dennis et al. *Biochemistry* 2001, 40, 9513-9521, or (d) SAEWEVLCWTWEGCGSVGLV (SEQ ID NO 151), SEEWEVLCWTWEDCRLEGLE (SEQ ID NO 152), EGTLCDDPRIDRWYCMFSGV (SEQ ID NO 153), and WEVLCWTWETCER (SEQ ID NO 154) described in Roberge et al. *Bioechemistry* 2001, 30, 9522-9531.

Similar techniques can be used to prepare further homing peptides for Factor VIII and Factor VII and also to prepare new homing peptides for other target proteins of interest. Examples of peptides binding to Fab/IgG1 are e.g., described in A. Arouri et al., *Eur. Biophys. J.*, 2007, 36, 647-660, DOI: 10.1007/s00249-007-0140-8; H. Yang et al. *J. Peptide Res.*, 2006, 66 (Suppl. 1), 120-137. doi:10.1111/j.1747-0285.2006.00342.x and references therein.

Linker

The term "linker" as used herein refers to any moiety that is capable of connecting the homing peptide (P) to the ester or carbamate group attached to the substituent (G). The linker is preferably relatively chemically inert, so that it is not chemically modified at any point during the method of the invention. The linker preferably has a molecular weight of 50 to 2000. When q is two or more, then the linker must have two or more sites where the G-C(O)—O— moiety can be attached. Thus, if q is one, the linker L is a diradical, if q is two, the linker L is triradical, and likewise for higher values of q.

The bond between the linker (L) and the homing peptide (P) is preferably an amide bond. In an embodiment, the —C(O)— portion of the amide bond is part of the linker (L) and the —NH— portion of the amide bond is part of the homing peptide (P). In an alternative embodiment, the —NH— portion of the amide bond is part of the linker (L) and the —C(O)— portion of the amide bond is part of the homing peptide (P).

The G-C(O)—O— moiety is preferably attached to a carbon atom on the linker (L). Such a carbon atom is typically a carbon atom in alkylene group or a carbon atom in an aryl group, such as a phenyl group.

The linker (L) is typically a linear or branched alkylene chain which is interrupted (a) by one or more groups selected from —O—, —S—, —NH—, —C(O)—, unsubstituted or substituted $C_6$-$C_{10}$ aryl groups and

, and (b) optionally by one or more peptides comprising 1 to 15 amino acids. The moiety

indicates a trivalent nitrogen atom in the alkylene chain. As will be apparent to one skilled in the art, an interrupted alkylene chain carrying such a moiety will be branched.

Preferably, the linker is a group of formula (II):

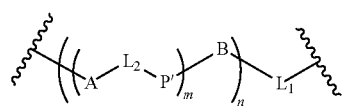

(II)

wherein:
$L_1$ represents a straight or branched $C_1$ to $C_{25}$ alkylene which is interrupted by one or more —O—, —NH—, —C(O)— or

groups, said alkylene being unsubstituted or substituted by one or more halogen atoms,
$L_2$ represents a direct bond or a said straight or branched $C_1$ to $C_{25}$ alkylene chain,
P' represents a direct bond or a peptide comprising 1 to 20 amino acids,
A represents a direct bond or a group of formula (III):

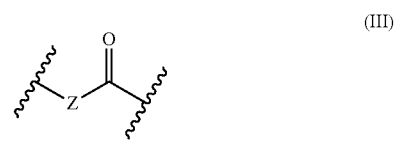

(III)

wherein Z represents a $C_6$ to $C_{10}$ arylene group which is unsubstituted or substituted with one or more nitro, $C_1$ to $C_6$ alkyl, $C_1$ to $C_6$ alkoxy, halogen or hydroxyl groups; a $C_1$ to $C_{10}$ alkylene group which is unsubstituted or substituted with one or more nitro, $C_1$ to $C_6$ alkoxy, halogen or hydroxyl groups; or a $C_3$ to $C_9$ cycloalkylene group which is unsubstituted or substituted with one or more nitro, $C_1$ to $C_6$ alkoxy, halogen or hydroxyl groups,
B represents a direct bond or a group of formula (IVa) or (IVb):

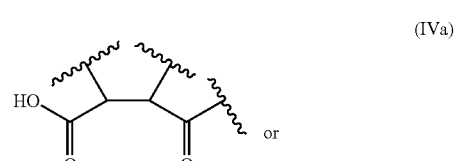

(IVa)

or

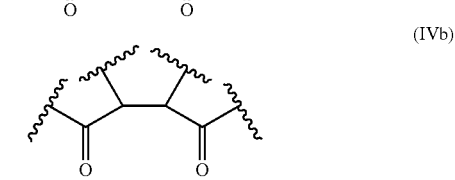

(IVb)

m is an integer from 1 to 3, and
n is an integer from 1 to 3.
When n or m is greater than one, such that more than one A, $L_2$, P' or B is present in the linker (L), each A, $L_2$, P' or B is the same or different.

$L_1$ is preferably a straight or branched unsubstituted $C_5$ to $C_{18}$ alkylene chain which is interrupted by one or more groups selected from —O—, —NH—, —C(O)— and

.

More preferably $L_1$ is a straight unsubstituted $C_5$ to $C_{18}$ alkylene chain interrupted by 0 to 6 —O—, 0 to 4 —NH—, 1 to 2 —C(O)— and 0 to 2

.

Typically $L_1$ terminates with a —C(O)— group at the end attached to the homing peptide (P); said —C(O)— group forms part of an amide bond to the homing peptide (P). Alternatively, $L_1$ terminates with a —NH— group at the end attached to the homing peptide (P); said —NH— group forms part of an amide bond to the homing peptide (P).

When $L_1$ is interrupted by one or more

groups, the branching introduced by this group allows an n value of 2 or more, typically 2. A value of n greater than 1 also arises from other forms of branching, for example branching in the alkylene chain. It will be apparent to one skilled in the art that: when n is 1, $L_1$ is a diradical; when n is 2, $L_1$ is a triradical; when n is 3, $L_1$ is a tetraradical.

$L_1$ is most preferably one of the following groups of formula (Va), (Vb), (Vc), (Vd) or (Ve):

In all of the above groups of formula (V), an amide bond is typically formed between the —C(O)— moiety on the right hand side of the compound of formula (V) and a terminal —NH-moiety on the homing peptide (P).

$L_2$ is preferably a direct bond or a straight unsubstituted $C_1$ to $C_{10}$ alkylene chain which is interrupted by one or more groups selected from —O—, —NH— and —C(O)—. Thus, when $L_2$ is not a direct bond, it represents a diradical. Typically each said $C_1$ to $C_{10}$ alkylene chain is interrupted by 0 to 6-O—, 1 to 4 —NH— and 0 to 2 —C(O)—. More preferably $L_2$ is a direct bond or a straight or branched $C_2$ to $C_6$ alkylene chain interrupted by 0 to 3 —O—, 1 to 2 —NH— and 0 to 1 —C(O)—. Most preferably, $L_2$ is a direct bond or a group of formula (VIa) or (VIb):

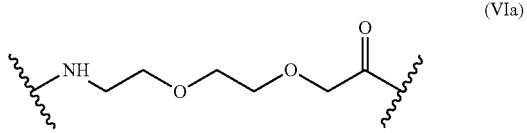

(VIa)

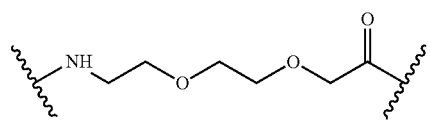

(Va)

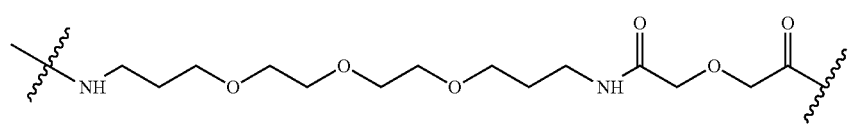

(Vb)

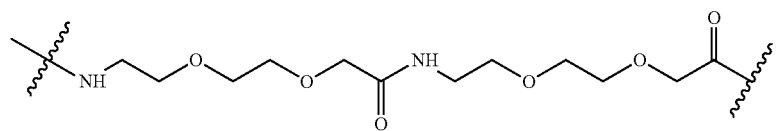

(Vc)

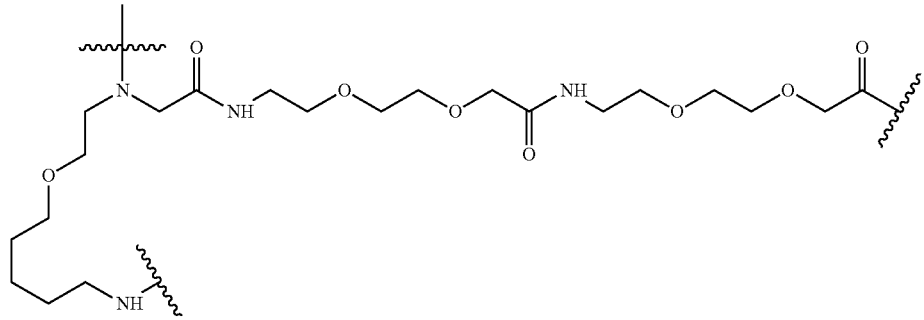

(Vd)

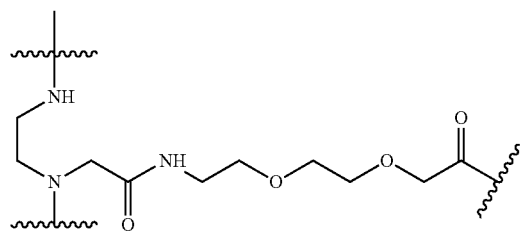

(Ve)

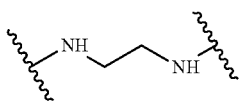
(VIb)

P' preferably represents a direct bond or a peptide consisting of 1 to 8 amino acids, preferably 1 to 3 amino acids. Said peptide P' is a diradical. When P' is not a direct bond, the peptide is generally included in the linker to improve the solubility of the targeted reagent in water. The amino acids present in the peptide P' are preferably polar or charged amino acids, for example acidic or basic amino acids.

Typically the peptide P' consists of 1 to 8 polar or charged amino acids, for example 1 to 3. Preferred polar or charged amino acids include serine (S), threonine (T), tyrosine (Y), histidine (H), lysine (K), arginine (R), aspartic acid (D), asparagines (N), glutamic acid (E) and glutamine Q. Alternatively, unnatural polar or charged amino acids could be used. Said peptide P' preferably comprises one or more of: glutamic acid (E), tryptophan (W) and tyrosine (Y). More preferably, said peptide P' comprises at least one glutamic acid (E) residue. Most preferably said peptide P' has a sequence E, ERE or WEY.

In the groups of formula (IVa) and (IVb), the carbonyl carbon on the right hand side of the groups of formula (IVa) and (IVb) is attached to $L_1$, typically forming an amide bond with a moiety —NH— from $L_1$. The —CH— radicals in the groups of formula (IVa) and (IVb) are typically attached to oxygen atoms, preferably to —OC(O)G moieties. As the skilled person will appreciate, this moiety is based on the tartrate group. The carbonyl carbon on the left hand side of the group of formula (IVb) is typically attached to a moiety —NH—, forming an amide bond. Said moiety —NH— is preferably from the moiety $L_2$, for example when $L_2$ represents a group of formula (VIb).

When B represents a group of formula (IVa) or (IVb), m is greater than 1. When B is a group of formula (IVa), m equals 2. When B is a group of formula (IXb), m equals 3. As the skilled person will appreciate the group of formula (IVa) is a triradical and the group of formula (IVb) is a tetratradical. When B is a group of formula (IVa) or (IVb), A is typically a direct bond.

In the group of formula (III):

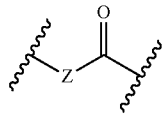
(III)

Z preferably represents a phenylene group which is unsubstituted or substituted by one or two halogen atoms, nitro groups or $C_1$ to $C_4$ alkyl groups, or a $C_1$ to $C_4$ alkylene group which is unsubstituted or substituted with one or two halogen atoms. More preferably Z represents an unsubstituted phenylene ring; a phenylene ring substituted by one nitro group; or a methylene or ethylene group.

When m and n are greater than 1, each A, $L_2$, D and B is the same or different. Thus, q in formula (I) preferably takes the values 1, 2, 3, 4, 6 and 9, more preferably 1, 2, 3 or 4, most preferably 1. The bonds linking $L_2$, P', B and $L_1$ are preferably amide bonds Preferred non-branched linkers (diradicals) are provided when:
$L_2$, P' and B are direct bonds, A is not a direct bond and m and n are both 1, such that the linker (L) is represented by: -$AL_1$-.
$L_2$ and B are direct bonds, A and P' are not direct bonds and m and n are both 1, such that the linker (L) is represented by: -AP'$L_1$-.
B is a direct bond, A, $L_2$ and P' are not direct bonds and m and n are both 1, such that the linker (L) is represented by: -$AL_2$P'$L_1$-.

Preferred branched linkers (triradicals, tetraradicals and pentaradicals respectively) are provided when:
B and $L_2$ are direct bonds, P' is not a direct bond, n is 2 and m is 1, such that the linker (L) is represented by: (-AP')-2-$L_1$-.
$L_2$, P' and A are direct bonds, B is not a direct bond, n is 1 and m is 2, such that the linker (L) is represented by:

P' is a direct bond, B is not a direct bond, n is 1 and m is 3. There are thus three branches in this linker, two having A and $L_2$ as direct bonds and one having A and $L_2$ not as direct bonds, such that the linker (L) is represented by:

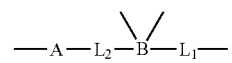

$L_2$, P' and A are direct bonds, B is not a direct bond, n is 2 and m is 2, such that the linker (L) is represented by:

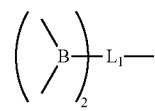

In a further embodiment, the linker (L) contains a moiety of formula (IVa) and a moiety of formula (IVb), and thus typically in this embodiment the linker (L) is represented by:

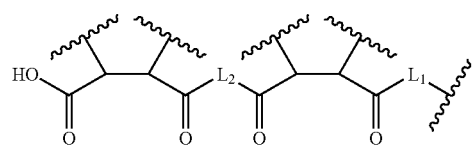

Substituents (G)
The substituent (G) refers to either (i) a substituent capable of subsequent modification ($G_1$), or (ii) a substituent that increases the plasma half-life of the protein ($G_2$).

Typically the targeted reagent carries one or two substituents (G). However, the targeted reagent may carry up to nine substituents (G), for example three or four. When there are two or more substituents (G), each substituent (G) is the same or different. For example, said substituents (G) may be a mixture of $G_1$ substituents and $G_2$ substituents. Further, when there is more than one $G_1$ or $G_2$ substituent, each $G_1$ or $G_2$ is the same or different. Preferably, however, each substituent is the same.

Substituents Capable of Subsequent Modification ($G_1$)

A substituent capable of subsequent modification ($G_1$) is a substituent that is used to selectively introduce a further substituent (R) into the protein, by reacting a protein carrying said substituent $G_1$ with a modifying reagent carrying the substituent R. The reactivity of the substituent $G_1$ and the modifying reagent carrying the substituent R is chosen such that when a modifying reagent carrying the substituent R reacts with a protein carrying the substituent $G_1$, the modifying reagent carrying the substituent R only reacts with the substituent $G_1$ on the protein. As a result, the substituent R is typically only introduced in regions of the protein where the substituent $G_1$ is present and the substituent R is typically not introduced into any other regions of the protein. In other words, a substituent R is typically only introduced at sites proximal to the binding site of the homing peptide on the target protein.

Typically, the substituent $G_1$ comprises an aldehyde, a ketone, an acetal, a hemiacetal, an azide, an alkyne, a pyridyl disulfide, an alkoxyamine or any derivative thereof. Preferably the substituent $G_1$ comprises an azide, an acetal, a hemicetal, or a ketone. The ketone is preferably an α,β-unsaturated carbonyl. The remaining portions of the substituent $G_1$ are typically unreactive, with the function of connecting the ketone, acetal, hemiacetal, azide, alkyne, pyridyl disulfide, alkoxyamine or derivative thereof initially to (i) the carbonyl carbon of the ester or carbamate of the targeted reagent, and subsequently to (ii) the target protein. Thus, the remaining portions of the substituent $G_1$ typically comprise unsubstituted or substituted, straight or branched alkylene moieties, unsubstituted or substituted cycloalkylene moieties, unsubstituted or substituted arylene moieties, tertiary amine moieties, unsubstituted or substituted alkenyl moieties, or any combination thereof. Preferred substituents for the above groups are halogen atoms, $C_1$ to $C_6$ alkyl, $C_1$ to $C_4$ alkoxy and nitro groups. Halogen atoms are most preferred substituents. The substituent $G_1$ typically has a molecular weight of 25 to 500.

A substituent $G_1$ comprising an aldehyde or a ketone is typically a saturated ketone of formula (VIIa):

(VIIa)

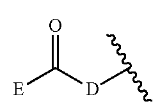

wherein:

D represents a straight or branched $C_1$ to $C_{10}$ alkylene which is unsubstituted or substituted by one or more halogen atoms; or a $C_6$ to $C_{10}$ arylene which is unsubstituted or substituted by one or more halogen atoms, $C_1$ to $C_6$ alkyl, $C_1$ to $C_6$ alkoxy or nitro groups; and E represents hydrogen, a straight or branched $C_1$ to $C_{10}$ alkyl which is unsubstituted or substituted by one or more halogen atoms; or a $C_6$ to $C_{10}$ aryl which is unsubstituted or substituted by one or more halogen atoms, $C_1$ to $C_6$ alkyl, $C_1$ to $C_6$ alkoxy or nitro groups.

Preferably D represents a straight or branched $C_2$ to $C_6$ alkylene which is unsubstituted; or a phenylene which is unsubstituted or substituted by one or more halogen atoms; and E represents a straight or branched $C_1$ to $C_6$ alkyl which is unsubstituted or substituted by one or more halogen atoms; or a $C_6$ to $C_{10}$ aryl which is unsubstituted or substituted by one or more halogen atoms, $C_1$ to $C_6$ alkyl, $C_1$ to $C_6$ alkoxy or nitro groups.

More preferably, D represents a straight or branched $C_2$ to $C_4$ alkylene which is unsubstituted and E represents a straight or branched $C_1$ to $C_4$ alkyl which is unsubstituted.

Alternatively, a substituent $G_1$ comprising a ketone is preferably an α,β-unsaturated carbonyl. A substituent $G_1$ comprising an α,β-unsaturated carbonyl group is typically a group of formula (VIIb):

(VIIb)

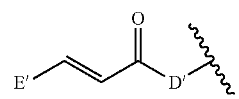

wherein either:

D' represents straight or branched $C_2$ to $C_{10}$ alkylene which is unsubstituted or substituted by one or more halogen atoms, and E' represents hydrogen, straight or branched $C_1$ to $C_6$ alkyl which is unsubstituted or substituted by one or more halogen atoms, —C(O)—($C_1$ to $C_6$ alkyl) or $C_6$ to $C_{10}$ aryl which is unsubstituted or substituted by one or more halogen atoms, $C_1$ to $C_6$ alkyl, $C_1$ to $C_6$ alkoxy or nitro groups; or D' represents $—(CH_2)_{2-10}—N—$ moiety and E' represents C═O and the nitrogen of D is attached to E' to form a 5 membered ring, for example with when D' represents-$(CH_2)_2—N—$:

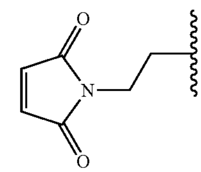 [SMILES: *CCN1C(=O)C=CC1=O]

In the above structure, the $—(CH_2)_{2-10}—$ alkylene chain is unsubstituted or substituted by one or more halogen atoms. Preferably it is an unsubstituted $—(CH_2)_{2-6}—$ moiety, more preferably unsubstituted $—(CH_2)_2—$ as depicted above.

Preferably D' represents straight or branched $C_2$ to $C_6$ alkylene which is unsubstituted and E' represents hydrogen, straight or branched $C_1$ to $C_4$ alkyl which is unsubstituted, or phenyl which is unsubstituted or substituted by one or more halogen atoms; or D' and E' form the cyclic structure described above.

Alternatively, a substituent $G_1$ comprising an α,β-unsaturated carbonyl group is preferably a group of formula (VIIc):

(VIIc)

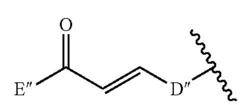

wherein D" represents straight or branched $C_2$ to $C_{10}$ alkylene which is unsubstituted or substituted by one or more halogen atoms, and E" represents straight or branched $C_1$ to $C_6$ alkyl which is unsubstituted or substituted by one or more halogen atoms, or $C_6$ to $C_{10}$ aryl which is unsubstituted or substituted by one or more halogen atoms, $C_1$ to $C_6$ alkyl, $C_1$ to $C_6$ alkoxy or nitro groups.

Preferably D" represents straight or branched $C_2$ to $C_6$ alkylene which is unsubstituted and E" represents, straight or branched $C_1$ to $C_4$ alkyl which is unsubstituted or phenyl which is unsubstituted or substituted by one or more halogen atoms.

A substituent $G_1$ comprising an acetal or hemiacetals is typically a group of formula (VIII):

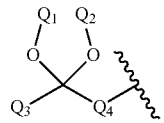
(VIII)

wherein:

$Q_1$ represents a straight or branched $C_1$ to $C_{10}$ alkyl which is unsubstituted or substituted by one or more halogen atoms, or a $C_6$ to $C_{10}$ aryl which is unsubstituted or substituted by one or more halogen atoms, $C_1$ to $C_6$ alkyl, $C_1$ to $C_6$ alkoxy or nitro groups;

$Q_2$ represents a hydrogen atom, a straight or branched $C_1$ to $C_{10}$ alkyl which is unsubstituted or substituted by one or more halogen atoms, or a $C_6$ to $C_{10}$ aryl which is unsubstituted substituted by one or more halogen atoms, $C_1$ to $C_6$ alkyl, $C_1$ to $C_6$ alkoxy or nitro groups; or $Q_1$ and $Q_2$ together form a straight $C_2$ to $C_5$ alkylene which is unsubstituted or substituted by one or more halogen atoms, said alkylene moiety forming a cyclic structure together with the —O—C—O— moiety;

$Q_3$ represents a hydrogen atom, a straight or branched $C_1$ to $C_{10}$ alkyl which is unsubstituted or substituted by one or more halogen atoms, or a $C_6$ to $C_{10}$ aryl which is unsubstituted substituted by one or more halogen atoms, $C_1$ to $C_6$ alkyl, $C_1$ to $C_6$ alkoxy or nitro groups; and $Q_4$ represents a $C_1$ to $C_{10}$ alkylene which is unsubstituted or substituted by one or more halogen atoms.

As the skilled person will appreciate, group of formula (VIII) is a hemiacetal when $Q_2$ is hydrogen and an acetal when $Q_2$ is not hydrogen. The acetal or hemiacetal is derived from an aldehyde when $Q_3$ is hydrogen. The acetal or hemiacetal is derived from a ketone when $Q_3$ is not hydrogen. Hemiacetals are less stable than acetals, and thus acetals are preferred. Both groups are easily deprotected under mild conditions to reveal the aldehyde or ketone functionality.

A substituent $G_1$ comprising an azide group is typically a compound of formula (IX):

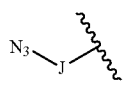
(IX)

wherein J represents a straight or branched $C_1$ to $C_{10}$ alkylene group which is unsubstituted or substituted by one or more halogen atoms; a $C_3$ to $C_8$ cycloalkylene group which is unsubstituted or substituted by one or more halogen atoms; or a $C_6$ to $C_{10}$ arylene group which is unsubstituted or substituted by one or more halogen atoms, $C_1$ to $C_6$ alkyl, $C_1$ to $C_4$ alkoxy, and nitro. When J represents a $C_1$ to $C_{10}$ alkylene group, the —$N_3$ is attached to a terminal or non-terminal carbon atom, preferably to a terminal carbon atom. Preferably J represents an unsubstituted $C_1$ to $C_6$ alkylene group or a phenylene group which is unsubstituted or substituted by one or two halogen atoms. Most preferably J represents an unsubstituted phenylene group and the —$N_3$ in the para position:

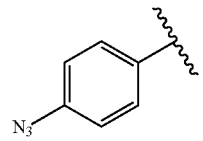

A substituent $G_1$ comprising an alkyne group is typically a straight or branched $C_2$ to $C_{10}$ alkynyl group, which is unsubstituted or substituted by one or more halogen atoms. Said alkynyl group comprises one or more carbon-carbon triple bond, preferably one carbon-carbon triple bond. Preferably an alkynyl group is an unsubstituted straight or branched $C_2$ to $C_7$ alkynyl group. Examples of alkynyl groups are straight or branched ethynyl, propynyl, butynyl, pentynyl, hexynyl or heptynyl. Preferably the triple bond is the terminal bond in the alkynyl group.

A substituent $G_1$ comprising a pyridyl disulfide group is typically a group of formula (Xa), (Xb) or (Xc):

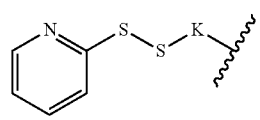
(Xa)

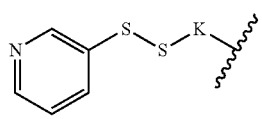
(Xb)

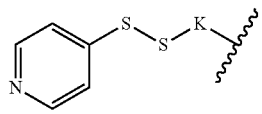
(Xc)

wherein K is a straight or branched $C_1$ to $C_{10}$ alkylene group which is unsubstituted or substituted by one or more halogen atoms. K is preferably an unsubstituted straight or branched $C_1$ to $C_6$ alkylene group. The pyridyl disulfide group is attached to a terminal or non-terminal carbon atom in the alkylene group, preferably to a terminal carbon.

A substituent $G_1$ comprising an alkoxyamine group is typically a group of formula (XI)

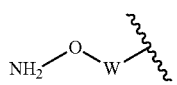
(XI)

wherein W is a straight or branched $C_1$ to $C_{10}$ alkylene group which is unsubstituted or substituted by one or more halogen atoms. W is preferably an unsubstituted straight or branched $C_1$ to $C_6$ alkylene group. The alkoxyamine group is attached to a terminal or non-terminal carbon atom in the alkylene group, preferably to a terminal carbon.

Introduction of a Substituent R

The substituent capable of subsequent modification ($G_1$) can be used to introduce a further substituent (R) into the protein at a site proximal to the binding site of the homing peptide on the target protein. The substituent (R) is preferably a substituent that increases the plasma half-life of the target protein.

Proteins typically have a number of clearance sites. As used herein, the term "clearance site" is defined as a region on the protein molecule that is recognized by the physiological machinery responsible for degradation of the protein. Thus, the half-life of a protein can be increased by disrupting said clearance sites by introducing a substituent into the protein. A "disrupted clearance site" is defined as a clearance site on the protein molecule that exhibits reduced binding to its cognate receptor or interaction partner as a result of above-mentioned modification.

Thus, the plasma half-life of a protein can be improved by introducing one or more moieties into the protein that disrupt clearance sites. Such moieties typically hide, mask or eclipse one or more clearance sites on the protein. Thus, in one embodiment, the invention provides a protein derivative with an improved plasma half-life. The improvement is with respect to the corresponding unmodified protein.

The plasma half-life of a protein or a protein derivative is determined by measuring the in vivo plasma half-life. The in vivo plasma half-life of proteins varies considerably. For example, human Factor VIII has a plasma half-life of about 12 to 14 hours. "In vivo plasma half life" of a protein is the time at which 50% of the protein or protein derivative circulates in the plasma or bloodstream prior to being cleared. Determination of plasma half-life is typically simpler than determining functional half-life and the magnitude of plasma half-life is usually a good indication of the magnitude of functional in vivo half-life. Alternative terms to plasma half-life include serum half-life, circulating half-life, circulatory half-life, serum clearance, plasma clearance, and clearance half-life.

The term "increased" as used in connection with the plasma half-life is used to indicate that the relevant half-life of the protein derivative is statistically significantly increased relative to that of the unmodified protein, as determined under comparable conditions. For instance the relevant half-life may be increased by at least about 25%, such as by at least about 50%, e.g., by at least about 100%, 150%, 200%, 250%, or 500%. In one embodiment, the protein derivatives of the present invention exhibit an increase in half-life of at least about 5 hours, preferably at least about 24 hours, more preferably at least about 72 hours, and most preferably at least about 7 days, relative to the half-life of the parent protein.

The term "parent protein" as used herein refers to the specific protein from which the protein derivative in question is derived.

Measurement of in vivo plasma half-life can be carried out in a number of ways as described in the literature. An increase in in vivo plasma half-life may be quantified as a decrease in clearance (CL) or as an increase in mean residence time (MRT). Protein derivatives of the present invention for which the CL is decreased to less than 70%, such as less than 50%, such than less than 20%, such than less than 10% of the CL of the parent protine as determined in a suitable assay is said to have an increased in vivo plasma half-life. Protein derivatives of the present invention for which MRT is increased to more than 130%, such as more than 150%, such as more than 200%, such as more than 500% of the MRT of the parent protein in a suitable assay is said to have an increased in vivo plasma half-life. Clearance and mean residence time can be assessed in standard pharmacokinetic studies using suitable test animals. It is within the capabilities of a person skilled in the art to choose a suitable test animal for a given protein. Tests in human, of course, represent the ultimate test. Typically, and as an example, the mice, rats, dogs, monkeys or pigs are in injected with the compound of interest. The amount injected depends on the test animal. Subsequently, blood samples are taken over a period of one to five days as appropriate for the assessment of CL and MRT. The blood samples are conveniently analysed by ELISA techniques.

Typically, the substituent R comprises: a bisphosphonate, a substituent that binds to platelets or endothelial cells, an antibody, a hydrophilic polymer, albumin or an albumin binder.

As used herein, the term "bisphosphonate" typically refers to a substituent comprising a diradical selected from:

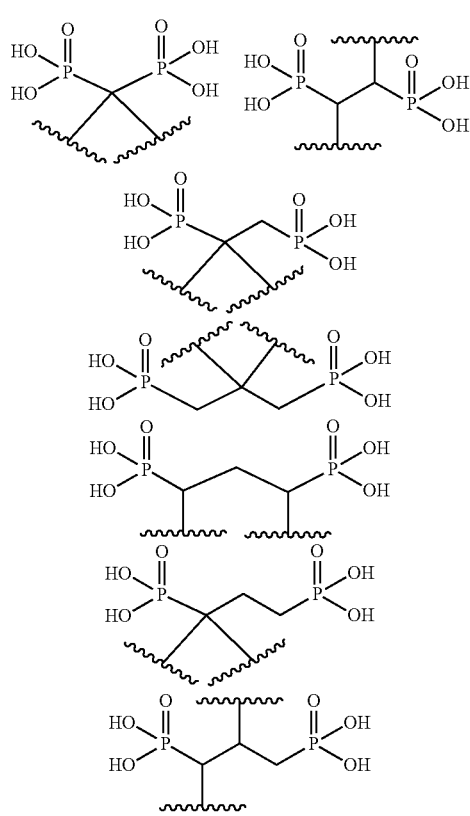

Such moieties typically have a high binding affinity for calcium.

As used herein, the term "substituents that bind to platelets or endothelial cells" typically relates to peptides containing the sequence RGD, for example echistatin or fibrinogen or fragments thereof.

The term "antibody" as used herein covers intact monoclonal antibodies, polyclonal antibodies, multispecific antibodies (e.g specific antibodies) formed from at least two intact antibodies, and antibody fragments so long as they exhibit the desired biological activity. The antibody may be an IgM, IgG (e.g IgG1, IgG2, IgG3 or IgG4), IgD, IgA or IgE, for example. The term "antibody" includes antibody fragments, for example FC-fragments of antibodies or FAB-fragment of antibodies.

As used herein, the term "hydrophilic polymer" refers to poly(ethyleneglycols) (PEG), polysaccharides, copolymers of ethylene glycol, propylene glycols, poly(propylene glycols), PC, poly(sialic acid), poly(vinylpyrrolidone), poly(olefinic alcohol), poly(oxyethylated alcohols), poly(α-hydroxy acids), poly(vinylalcohol), polyphosphazene and polyoxazoline. Said hydrophilic polymer preferably has a mass of 0.3 to 150 kDa, more preferably 5 to 120 kDa.

The substituent R preferably comprises PEG. Thus, in one embodiment, the present invention provides a method for selectively PEGylating a protein. The term "PEG" as used herein refers to poly(ethylene glycol), also known as poly (ethylene oxide) (PEO) or polyoxyethylene (POE), are polyethers. PEG is prepared by polymerization of ethylene oxide and are commercially available over a wide range of molecular weights from 300 g/mol to 10,000,000 g/mol.

Different forms of PEG are also available dependent on the initiator used for the polymerization process. The most common form of PEG is a monofunctional methyl ether PEG (methoxypoly(ethylene glycol)), abbreviated mPEG.

PEGs are also available with different geometries, such as linear, and branched PEGs. PEG has the structure HO—$(CH_2—CH_2—O—)_n$—H, the molecular formula $C_{2n}H_{4n+2}O_{n+1}$, and the CAS number [25322-68-3]. The molar mass of course depends on n.

The numbers that are often included in the names of PEGs indicate their average molecular weights, e.g. a PEG with n=80 would have an average molecular weight of approximately 3500 daltons and would be labeled PEG 3500.

Most PEGs include molecules with a distribution of molecular weights, i.e. they are polydisperse. The size distribution can be characterized statistically by its weight average molecular weight ($M_w$) and its number average molecular weight (Mn), the ratio of which is called the polydispersity index ($M_w/M_n$) (see e.g. "Polymer Synthesis and Characterization", J. A. Nairn, University of Utah, 2003). $M_w$ and $M_n$ can be measured by mass spectroscopy.

The polydispersity index is accordingly a number which is greater than or equal to one, and it may also be estimated from Gel Permeation Chromatographic data. When the polydispersity index is 1, the product is monodisperse and is thus made up of compounds with a single molecular weight. When the polydispersity index is greater than 1 the polymer is polydisperse, and the polydispersity index tells how broad the distribution of polymers with different molecular weights is. The polydispersity index typically increases with the molecular weight of the PEG or mPEG.

For the present purposes, the terms "PEG" and "Peg" are used interchangeably and basically mean a radical or diradical comprising the structure

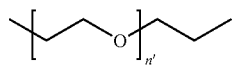

wherein n' is an integer larger than 1.

The term PEG is intended to indicate poly(ethylene glycol) as well as poly(ethylene glycol) monoalkyl ether, wherein alkyl indicates $C_{1-6}$alkyl, such as methyl, ethyl, propyl, butyl, pentyl and hexyl. Accordingly, in a preferred embodiment, Peg for use according to the invention is represented by the following formula:

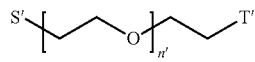

in which n' is an integer larger than 1, and S' and T' independently designates alkyloxy, hydroxy, or is absent. As explained above, a compound of this formula in which S' designates methyloxy and T' is absent is also referred to as mPEG.

The molecular weight of the PEG for use according to the invention preferably is between approximately 300 Da and approximately 150000 Da. The molecular weight of the Peg in kDa may be indicated in parentheses. By way of example, mPEG(30k) indicates poly(ethylene glycol) monomethyl ether with a molecular weight of approximately 30 kDa. This polymer may, by the way, be composed of approximately 680±100 ethylene glycol units. As another example, in mPEG (4k) n is 90 and the molecular weight is 3991 Da, i.e. approx 4 kDa. Likewise, mPEG(20k) has an average molecular weight of 20 kDa and an average n of 454.

The PEG for use according to the present invention may be linear, or branched. In particular embodiments the PEG for use according to the invention is a) polydisperse, or b) monodisperse. In particular embodiments, the polydispersity index of the Peg for use according to the invention is i) below 1.06, ii) below 1.05, iii) below 1.04, iv) below 1.03, or v) between 1.02 and 1.03.

The term "albumin" as used herein refers to serum albumin from blood serum, and includes human serum albumin as well as serum albumin from other sources. The term "albumin" as used herein includes any derivatives of albumin or modified versions of albumin.

The term "albumin binder" as used herein refers to any moiety capable of binding to albumin. The ability of a compound to bind to albumin may be determined as described in J. Med. Chem., 43, 2000, 1986-1992, which is incorporated herein by reference. In the present context, a compound is defined as binding to albumin if Ru/Da is above 0.05, such as above 0.10, such as above 0.12 or even above 0.15. Albumin binders are typically highly hydrophobic molecules, preferably derived from fatty acids. Thus, an albumin binder will preferably comprise a —$(CH_2)_{12}$— moiety. Other albumin binders include peptides such as cibachrome.

The methods, techniques and reaction conditions used to introduce the substituent (R) depend on a number of factors. Importantly, reaction conditions should be mild enough that the protein is not irreversibly damaged. Exact reagents will depend on, for example, the nature and reactivity of the substituent $G_1$ that has been introduced into the target protein and the modifying reagent carrying the substituent R. Further, the reactivity of the modifying reagent should be such that the modifying reagent only reacts with the substituent $G_1$ on the protein, and does not modify the remaining part of the protein in any way. Suitable techniques and reagents are known to those skilled in the art.

If $G_1$ comprises an aldehyde or a ketone, then a nucleophilic modifying reagent is typically used to introduce the substituent R. For example, if $G_1$ comprises an α,β-unsaturated carbonyl moiety, such as maleoyl, reactions of the following type using soft nucleophiles such as RSH are preferred for introducing a substituent (R), via conjugate addition:

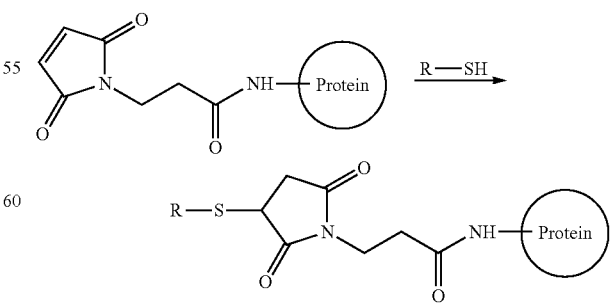

If $G_1$ comprises an azide moiety, standard techniques such as "click-chemistry" (triazole formation from the azide with an alkyne) or Staudinger-assisted reductive acylation (formation of amide via reaction with a phosphanyl-carboxylic acid derivative) are typically used to introduce a desired substituent.

If $G_1$ comprises a pyridine disulfide group, a nucleophile such as RSH is typically used to cleave the S—S bond, thereby forming a new bond disulphide bond between R and the protein:

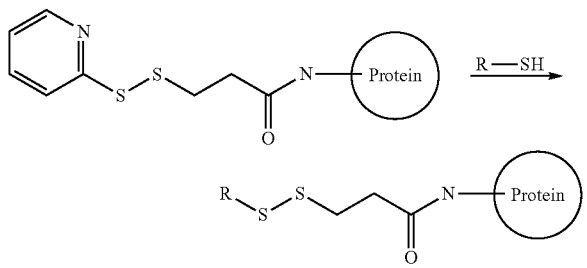

If $G_1$ comprises an alkoxyamine group, a reaction with an aldehyde of formula RCHO is typically used to introduce the substituent R:

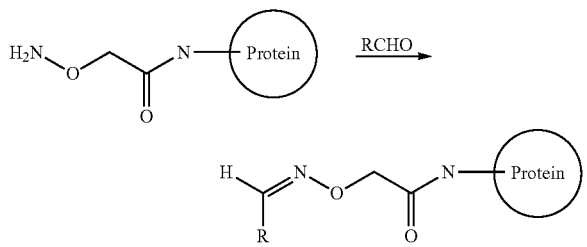

If $G_1$ comprises an alkyne, reactions known to those skilled in the art are used to introduce a substituent R. For example, standard techniques such as "click-chemistry" (triazole formation from the alkyne with an azide) may be used to introduce a desired substituent.

If $G_1$ comprises an acetal or hemiacetal, then a deprotection reaction, typically under mild conditions, is preferably used to reveal the aldehyde or ketone functionality. A ketone can then be used to introduce a substituent R, for example as set out above. A aldehyde typically reacts with a nucleophilic reagent to introduce the substituent R. For example, an alkoxyamine compound of formula R—O—NH$_2$ reacts with an aldehyde/ketone as follows:

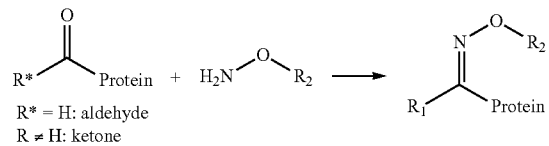

The above reactions are not intended to be limiting and a skilled person will be able to choose alternative techniques, reagents and reaction conditions, as necessary, for successful introduction of a substituent R.

Substituents that Increase the Plasma Half-Life of the Target Protein ($G_2$)

In an alternative embodiment, the present invention is used to introduce substituents that increase the plasma half-life of the target protein directly. The term "increase the plasma half-life" is as defined above. The substituent $G_2$ preferably comprises a bisphosphonate, a substituent that binds to platelets or endothelial cells, an antibody, a hydrophilic polymer (such as e.g. a poly sialic acid (PSA), polyethylene glycol (PEG), hydroxyl ethyl starch (HES), etc.), albumin, an Fc domain (optionally comprising mutations resulting in reduced effector functions), or an albumin binder such as e.g. a fatty acid or a fatty acid derivative, wherein these terms are as defined above. Preferably the substituent $G_2$ comprises PEG and thus, in one embodiment, the present invention provides a method for selectively PEGylating a protein.

Screening of Modified Proteins

The proteins modified using the reagents and techniques described above generally undergo subsequent screening to confirm whether essential biological activity has been affected. Preferably, the modified proteins of the invention have substantially the same as the activity parent protein. "Protein activity" is defined as the ability to perform the essential biological activities of the protein, such activities are well known to those skilled in the art. For example, "FVIII activity" is defined as the ability to function in the coagulation cascade, induce the formation of Factor Xa via interaction with Factor IXa on an activated platelet, and support the formation of a blood clot.

As used herein, the term "protein activity is substantially the same as the activity of the parent protein" mean that the activity of the modified protein is at least 20%, at least 30%, at least 40%, at least 50%, at least 60%, at least 70%, at least 80%, at least 90% such as at least 100% of that of the parent protein. The modified protein activity is in particular about 50 to about 75%, about 75 to about 85%, about 85 to about 95% and even more than 100% of that of parent protein. The specific screening assays will depend on the protein that has been modified. Suitable assays will be known to one skilled in the art in this field. Such subsequent screening steps allow modified proteins that have lost their essential biological activity to be identified.

Commercially available assay kits are typically used. For example, a chromogenic assay kit is generally used for the determination of Factor VIII activity in human plasma, blood fractions and purified preparations. Preferred kits are for the determination of Factor VIII activity Coamatic Chromogenic assay kit (Chromogenix, Milan, Italy) and CoaTest SP FVIII assay kit (Chromogenix, Milan, Italy).

Targeted reagents of formula (I) may be prepared by standard methods known to those skilled in the art.

Pharmaceutical Compositions

The modified proteins obtainable by the methods of the invention are useful in treatment of the human or animal body. Thus, the present invention also relates to pharmaceutical compositions comprising proteins obtainable by the methods of the invention. Typically said pharmaceutical compositions further comprise a pharmaceutically acceptable carrier or diluent.

A preferred pharmaceutically acceptable carriers or diluents is an aqueous buffered solution. Thus, the present invention relates to a pharmaceutical formulation comprising an aqueous solution of a modified protein of the invention and a buffer, wherein the modified protein is present in a concentration from 0.001 mg/ml or above, and wherein said formulation has a pH from about 2.0 to about 10.0.

Typically, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

Typically, the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19.sup.th edition, 1995.

Typically, the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 19.sup.th edition, 1995.

Typically, the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 19.sup.th edition, 1995.

Typically, the formulation further comprises a stabilizer. The use of a stabilizer in pharmaceutical compositions is well-known to the skilled person. For convenience reference is made to Remington: The Science and Practice of Pharmacy, 19.sup.th edition, 1995.

Typically, the pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or DL isomer) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, or nithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

Typically, the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation comprises a surfactant. The surfactant may be a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)—derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives (e.g. sodium tauro-dihydrofusidate etc.), long-chain fatty acids and salts thereof C6-C12 (eg. oleic acid and caprylic acid), acylcarnitines and derivatives, N.sup.alpha.-acylated derivatives of lysine, arginine or histidine, or side-chain acylated derivatives of lysine or ginine or histidine, or side-chain acylated derivatives of lysine or arginine, N.sup.alpha.-acylated derivatives of dipeptides comprising any combination of lysine, arginine or histidine and a neutral or acidic amino acid, N.sup.alpha.-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyltrimethylammonium bromide, cetylpyridinium chloride), non-ionic surfactants (eg. Dodecyl .beta.-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: The Science and Practice of Pharmacy, 19.sup.th edition, 1995.

It is possible that other ingredients may be present in the pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Parenteral administration of the pharmaceutical composition is typically performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration in the form of a nasal or pulmonal spray. As a still further option, the pharmaceutical compositions can also be adapted to transdermal administration, e.g. by needle-free injection or from a patch, optionally an iontophoretic patch, or transmucosal, e.g. buccal, administration.

The present invention is further illustrated by the following examples, which should not be construed as further limiting.

EXAMPLES

Identification of Homing Peptides

Solid phase libraries based on the one-bead one-peptide method were screened using 0.1 to 10 ug/ml of biotinylated FVIII in an incubation buffer (0.5% BSA, 25 mM TRIS, pH=7.4, 0.15M NaCl, 0.05% Tween20) for 1 to 2 hours. After incubation the library was washed with washing buffer (25 mM TRIS, pH=7.4, 0.15M NaCl, 0.05% Tween20) about 5 to 6 times with a volume corresponding to two resin volumes.

After washing the library was incubated with streptavidin-alkaline phosphatase (Strep-AP) 0.1 ug/ml in incubation buffer for about 15 to 30 minutes. After incubation, the library was washed with washing buffer and color buffer (50 mM TRIS, pH=8.8, 0.15M NaCl, 5 mM $MgCl_2$) was added together with 2 mg of 5-bromo-4-chloro-3-indolyl phosphate (BCIP). Staining of beads was allowed for 1 to 2 hours and the reaction was stopped by washing with 10% AcOH.

The darkest blue beads were retrieved from the library and sequenced using Edman sequencing on a Procise instrument from Applied Biosystems. In this way, peptides that bind to FVIII were identified.

Preparation of Targeted Reagents

Examples 1 to 20 relate to preparation of targeted reagents. A number of these targeted reagents have been designated as "reference", since the substituents that these targeted reagents introduce into proteins are not either substituents capable of subsequent modification ($G_1$) or modifying substituents ($G_2$). Rather, these substituents, which are derived from biotin and pyrene, labeled the region of the protein where the substituent was added.

Targeted Reagents without Branching or a Peptide (P') in the Linker

The following targeted reagents (Compounds 1 to 10) without branching or a peptide (P') in the linker were prepared.

Compound 1 (Reference for One Step Modification)

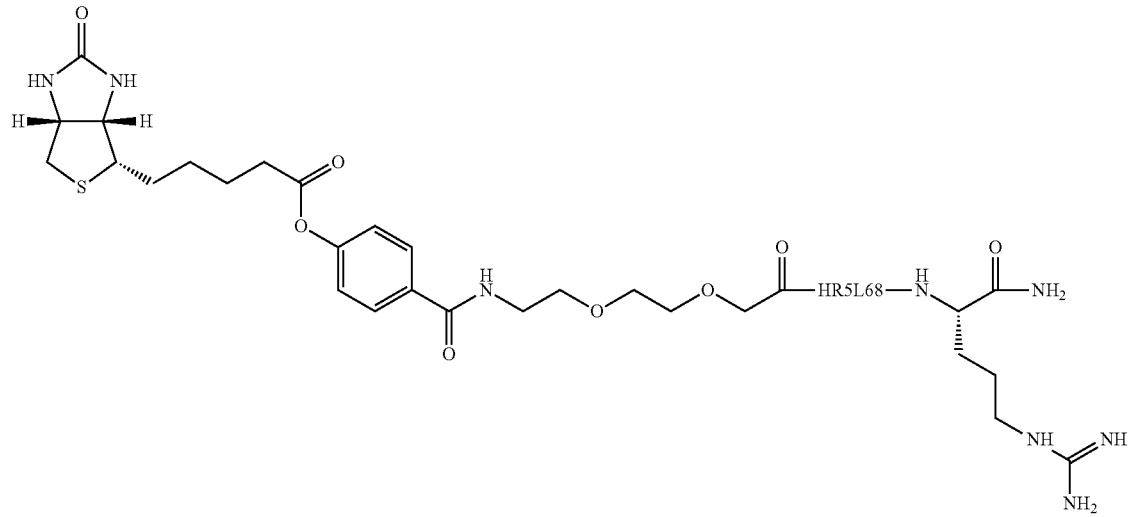

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A suspension of biotin in NMP (360 mg in 1 ml) was added to the resin. Once the solution was mixed with the resin, a solution of DIC and 4-(N,N-dimethylamino)pyridine in NMP was added. The mixture was shaken for 24 hours. The resin was washed and cleaved with 5% triethylsilane in TFA. The compound was triturated with diethyl ether.

LC-MS: 802 $(M+H)^{2+}$

Compound 2

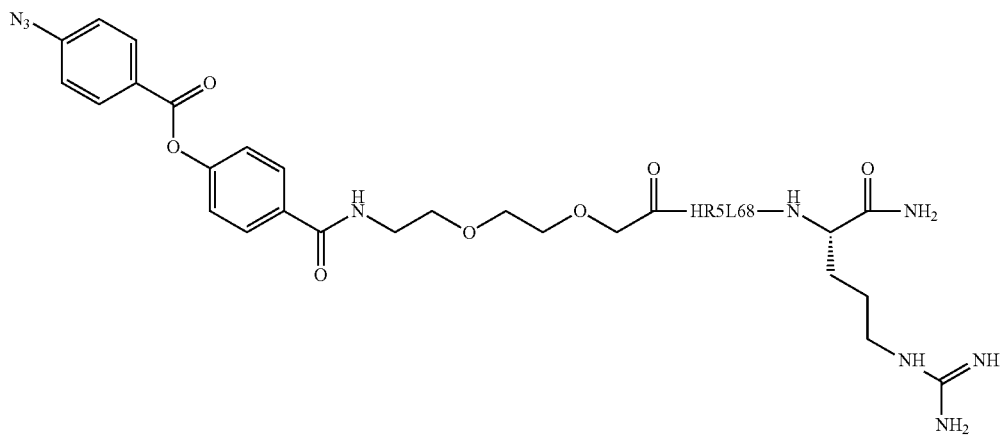

The same resin was used as for preparing Compound 1. After removal of the N-terminal Fmoc protecting group and subsequent washing of the resin, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A solution of 4-azidobenzoic acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 1522 (M+H)⁺

Compound 3 nol blue was used as monitoring reagent. The suspension was shaken until the colour indicated complete acylation (pale green). The resin was washed with NMP (5×10 ml). A solution of 4,7,10-trioxamidecan-1,13-diamine (25 eq) and PyBOP (5 eq) in NMP was added to the resin. The mixture was shaken for 2 hours. The resin was washed with NMP (5×10 ml). A mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

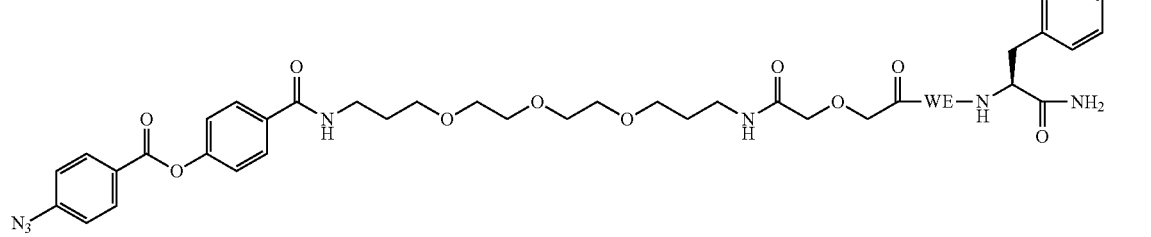

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a solution of diglycolic anhydride (10 eq) in NMP was added to the resin. Bromophe- The resin was washed with NMP, DCM with 5% acetic acid, and DCM. A solution of 4-azidobenzoic acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 1081 (M+H)⁺

Compound 4 (Reference for One Step Modification)

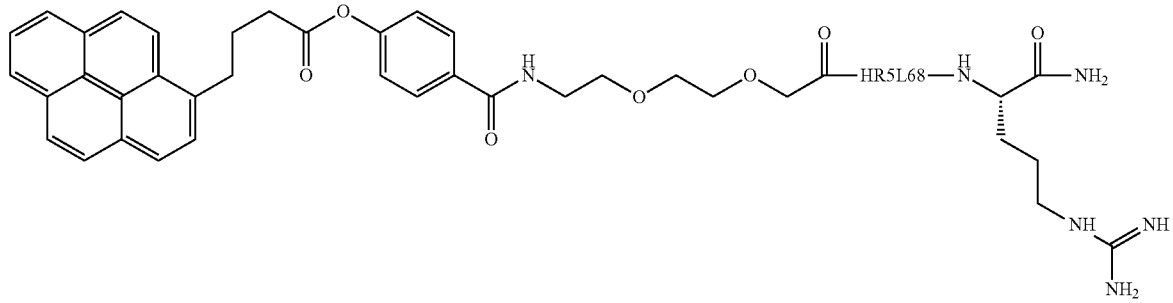

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-acetoxy-benzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A solution of 1-pyrenebutyric acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 825 $(M+H)^{2+}$

Compound 5 (Reference for One Step Modification)

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-hydroxy-3-nitrobenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

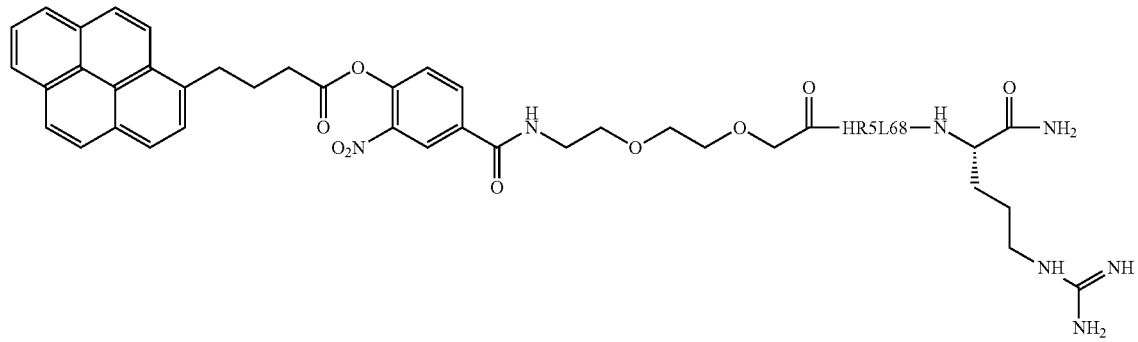

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The resin was washed with NMP, DCM with 5% acetic acid, and DCM. A solution of 1-pyrenebutyric acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 847 $(M+H)^{2+}$

Compound 6 (Reference for One Step Modification)

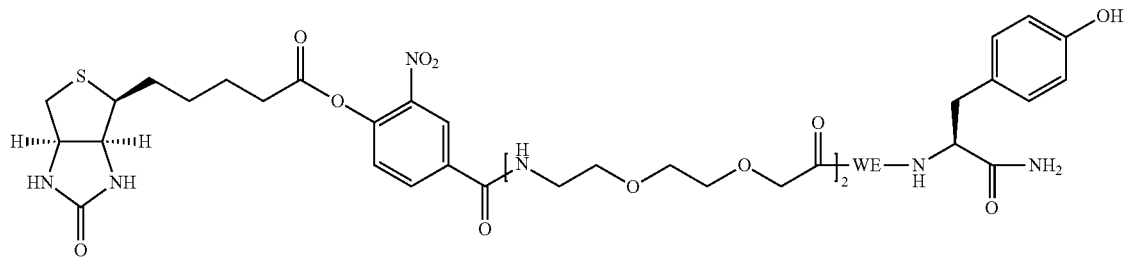

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-hydroxy-3-nitrobenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A suspension of biotin in NMP (360 mg in 1 ml) was added to the resin. Once the solution was mixed with the resin, a solution of DIC (10 eq) and 4-(N,N-dimethylamino)pyridine in NMP was added. The mixture was shaken for 24 hours. The resin was washed and cleaved with 5% triethylsilane in TFA. The compound was triturated with diethyl ether.

LC-MS: 1177 (M+H)⁺

Compound 7 acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. N-Maleoyl-β-alanine (4 eq) was suspended in DCM. N-methylimidazole (3 eq) was added. The mixture was shaken until the solution became clear. The solution was mixed with 1-(2-mesitylenesulfonyl)-3-nitro-1H-1,2,4-triaz-

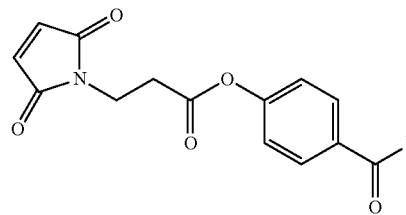 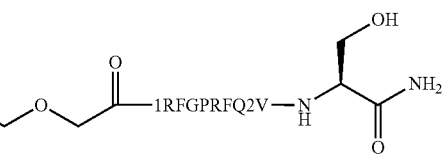

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin.

ole (MSNT) (4 eq). After complete dissolution, the mixture was mixed with the resin. The resulting mixture was shaken over night. The mixture was shaken for 24 hours. The resin was washed and cleaved with 5% water in TFA. The compound was triturated with diethyl ether.

LC-MS: 1792 (M+H)⁺

Compound 8

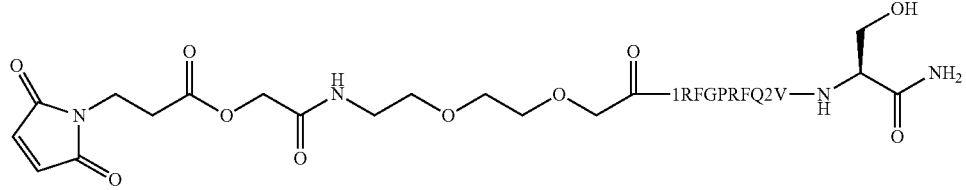

Bromophenol blue was used as monitoring reagent. The suspension was shaken until the colour indicated complete Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of acetoxyacetic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour. The resin was washed with NMP, DCM with 5% acetic acid, and DCM.

N-Maleoyl-β-alanine (4 eq) was suspended in DCM. N-methylimidazole (3 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 hours. The resin was washed and cleaved with 5% water in TFA. The compound was triturated with diethyl ether.

LC-MS: 1730 (M+H)+
Compound 9

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour. The resin was washed with NMP, DCM with 5% acetic acid, and DCM.

N-Maleoyl-β-alanine was suspended in DCM. N-methylimidazole (3 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 hours. The resin was washed and cleaved with 5% water in TFA. The compound was triturated with diethyl ether.

LC-MS: 1529 (M+H)+

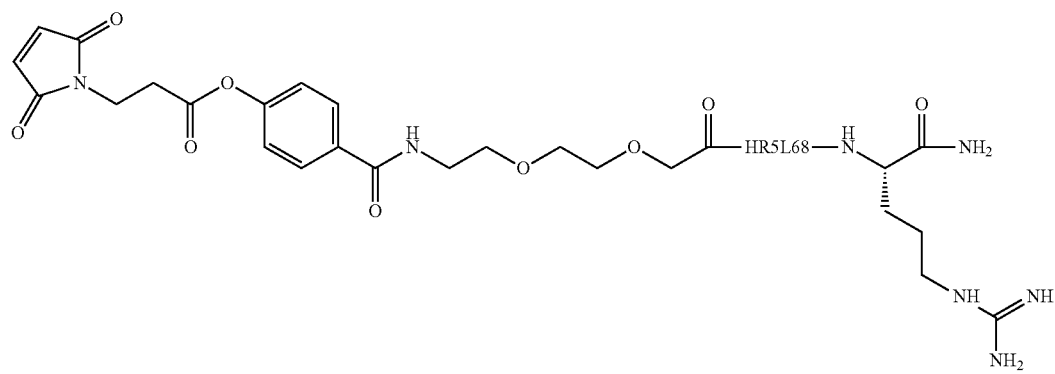

Compound 10

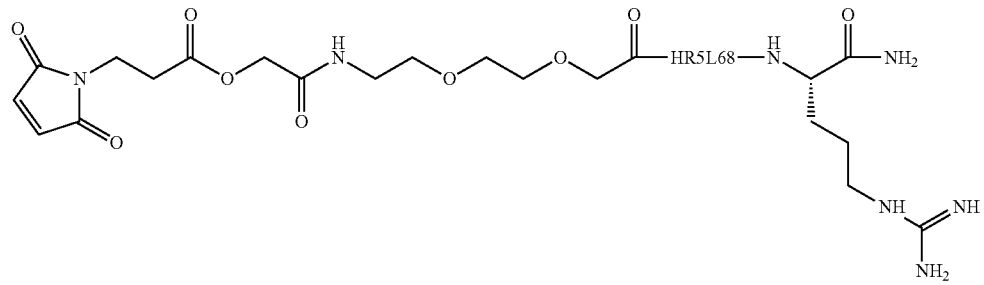

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of acetoxyacetic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml).

A mixture of tetrahydrofuran and saturated sodium methoxide in methanol (8:1) was added to the resin. The resulting mixture was shaken for 1 hour. The resin was washed with NMP, DCM with 5% acetic acid, and DCM.

N-Maleoyl-β-alanine (4 eq) was suspended in DCM. N-methylimidazole (3 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 hours. The resin was washed and cleaved with 5% water in TFA. The compound was triturated with diethyl ether.

LC-MS: 1467 (M+H)+

Targeted Reagents with a Peptide (P') in the Linker but No Branching

The following targeted reagents (Compounds 11 to 15) with a peptide (P') in the linker but no branching were prepared.

Compound 11

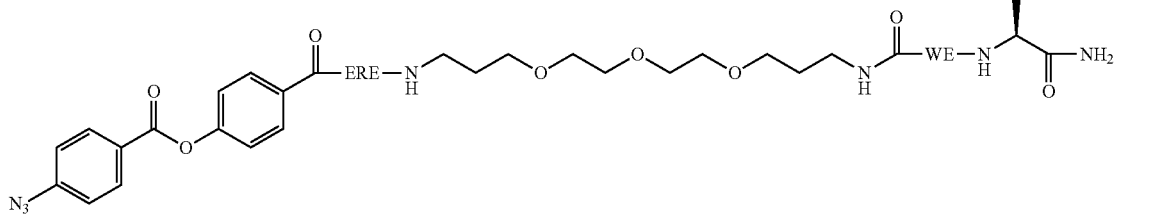

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a solution of diglycolic anhydride (10 eq) in NMP was added to the resin. Bromophenol blue was used as monitoring reagent. The suspension was shaken until the colour indicated complete acylation (pale green). The resin was washed with NMP (5×10 ml). A solution of 4,7,10-trioxamidecan-1,13-diamine (25 eq) and PyBOP (5 eq) in NMP was added to the resin. The mixture was shaken for 2 hours. The resin was washed with NMP (5×10 ml).

A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence ERE.

After removal of the Fmoc protecting group, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A solution of 4-azidobenzoic acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 747 (M+H)$^{2+}$

Compound 12 (Reference for One Step Modification)

After removal of the N-terminal Fmoc protecting group and subsequent washing of the resin, a solution of diglycolic anhydride (10 eq) in NMP was added to the resin. Bromophenol blue was used as monitoring reagent. The suspension was shaken until the colour indicated complete acylation (pale green). The resin was washed with NMP (5×10 ml). A solution of 4,7,10-trioxatridecan-1,13-diamine (25 eq) and PyBOP (5 eq) in NMP was added to the resin. The mixture was shaken for 2 hours. The resin was washed with NMP (5×10 ml).

A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence ERE.

After removal of the Fmoc protecting group, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring

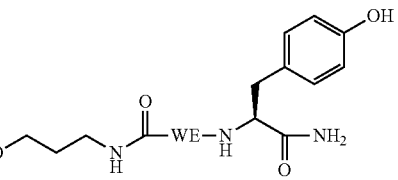

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A solution of 1-pyrenebutyric acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 810 (M+H)$^{2+}$

Compound 13

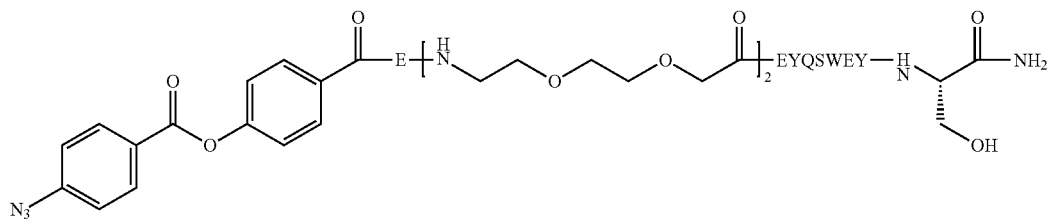

Repetitive cycles of the protocol described above were used for synthesising the sequence listed above.

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A solution of 4-azidobenzoic acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 888 (M+H)$^{2+}$

Compound 14 piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of 4-acetoxybenzoic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour. The resin was washed with NMP, DCM with 5% acetic acid, and DCM.

N-Maleoyl-β-alanine (3 eq) was suspended in DCM. N-methylimidazole (3 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 hours. The resin

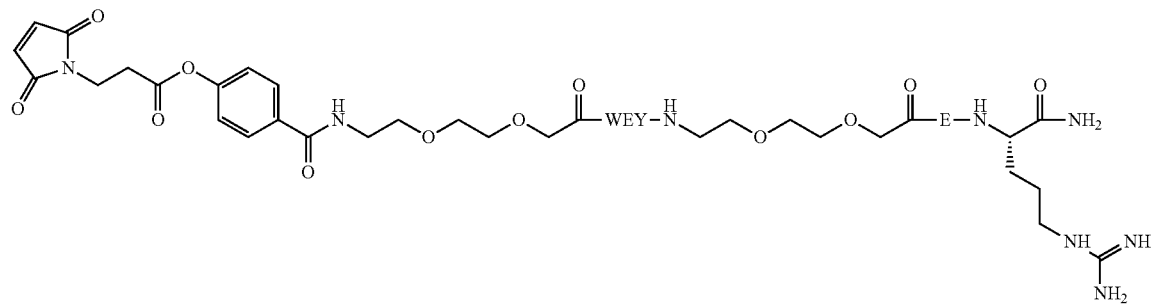

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hywas washed and cleaved with 5% water in TFA. The compound was triturated with diethyl ether.

LC-MS: 1344 (M+H)$^{+}$

Compound 15

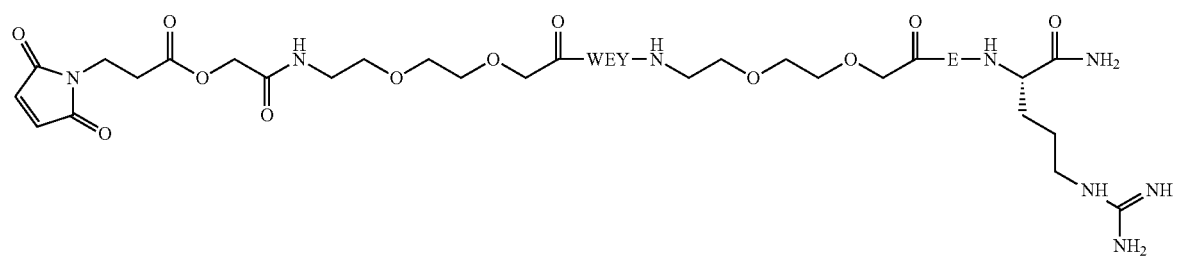

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of acetoxyacetic acid (4 eq), 7-aza-1-hydroxybentriazole (4 eq), and N,N'-diisopropylcarbodiimide (4 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour. The resin was washed with NMP, DCM with 5% acetic acid, and DCM.

N-Maleoyl-β-alanine (4 eq) was suspended in DCM. N-methylimidazole (4 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 hours. The resin was washed and cleaved with 5% water in TFA. The compound was triturated with diethyl ether.

LC-MS: 1280 (M+H)$^+$

Targeted Reagents with Branching Provided by a Tertiary Amine Moiety in the Linker The following targeted reagent (Compound 16) with branching provided by a tertiary amine moiety in the linker was prepared.

Compound 16

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a mixture of bromoacetic acid (10 eq) and N,N'-diisopropylcarbodiimide (5 eq) in NMP was added to the resin. Bromophenol blue was used as monitoring reagent. The suspension was shaken until the colour indicated complete acylation (yellow). The resin was washed with NMP (5×10 ml). A solution of 1,8-diamino-3,6-dioxaoctane (25 eq) in NMP. The mixture was shaken over night. The resin was washed.

A pre-mixed solution of Fmoc-amino acid (8 eq), 7-aza-1-hydroxybentriazole (8 eq), and N,N'-diisopropylcarbodiimide (8 eq) in NMP was added to the resin. Bromophenol blue was used as monitoring reagent. The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

A pre-mixed solution of 4-acetoxybenzoic acid (8 eq), 7-aza-1-hydroxybentriazole (8 eq), and N,N'-diisopropylcarbodiimide (8 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour.

The resin was washed with NMP, DCM with 5% acetic acid, and DCM. A solution of 4-azidobenzoic acid (10 eq), DIC (10 eq), and DMAP in NMP was added to the resin. The mixture was shaken for 24 hours. The resin was washed and cleaved with 5% triethylsilane in TFA. The compound was triturated with diethyl ether.

LC-MS: 1179 (M+H)$^{2+}$

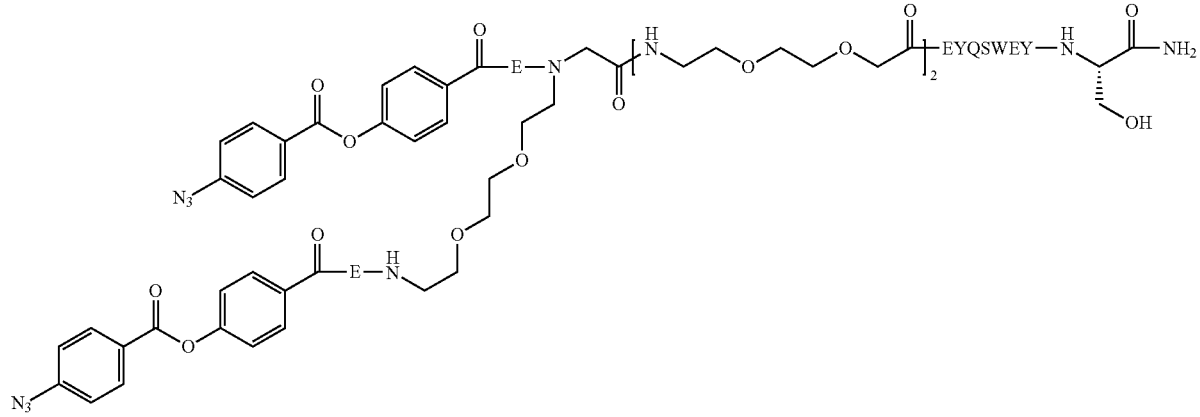

Compounds with Branching Provided by a Tartrate Moiety

The following targeted reagents (Compounds 17 to 20) with branching provided by a tartrate moiety in the linker were prepared.

Compound 17

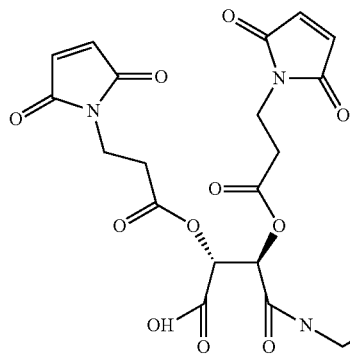

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute.

The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a solution of (+)-diacetoxy-L-tartaric anhydride (10 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour. The resin was washed with NMP, DCM with 5% acetic acid, and DCM.

N-Maleoyl-β-alanine (4 eq) was suspended in DCM. N-methylimidazole (3 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 hours. The resin was washed and cleaved with 5% water in TFA. The compound was triturated with diethyl ether.

LC-MS: 977 $(M+H)^{2+}$

Compound 18

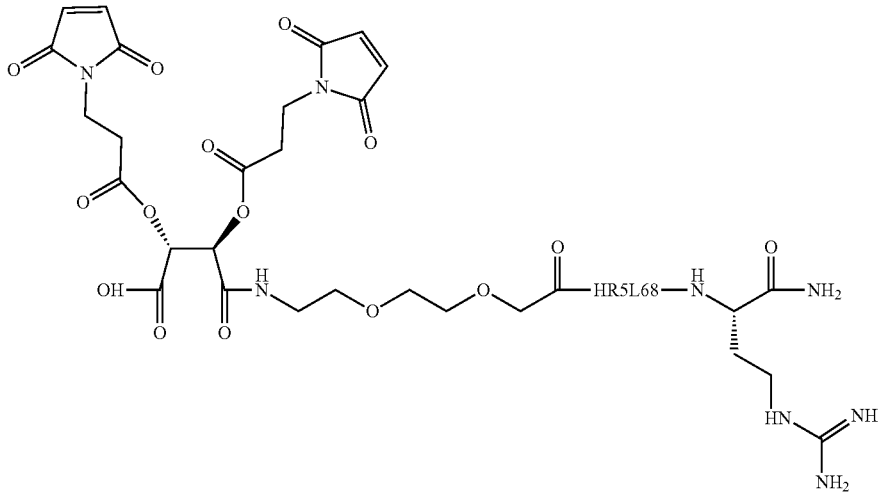

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a solution of (+)-diacetoxy-L-tartaric anhydride (10 eq) in NMP was added to the resin. Bromophenol blue was used as monitoring reagent. The suspension was shaken until the colour indicated complete acylation (pale green). The resin was washed with NMP (5×10 ml). A mixture of tetrahydrofuran and saturated sodium methoxide in methanol (8:1) was added to the resin. The resulting mixture was shaken for 1 hour. The resin was washed with NMP, DCM with 5% acetic acid, and DCM.

N-Maleoyl-β-alanine (4 eq) was suspended in DCM. N-methylimidazole (3 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 h. The resin was washed and cleaved with 5% water in TFA. The compound was triturated with diethyl ether.

LC-MS: 846 $(M+H)^{2+}$

Compound 19

(4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

A solution of bromoacetic acid (10 eq) and DIC (5 eq) in NMP was added to the resin. Bromophenol blue was used as monitoring reagent. The resin was washed with NMP after completion of the reaction. A solution of ethylene diamine in NMP was added. The mixture was shaken for 3 hours. The resin was washed.

A solution of (+)-diacetyl-L-tartaric anhydride (10 eq) in NMP was added to the resin. Bromophenol blue was used as monitoring reagent. The resin was washed with NMP after completion of the reaction. A solution of saturated sodium methoxide in methanol/THF (1:8) was added to the resin. The mixture was shaken for 1 hour. The resin was washed with NMP, 5% AcOH in NMP, NMP and DCM.

N-Maleoyl-β-alanine (4 eq) was suspended in DCM. N-methylimidazole (3 eq) was added. The mixture was shaken until the solution became clear. The solution was mixed with 1-(2-mesitylenesulfonyl)-3-nitro-1H-1,2,4-triaz-

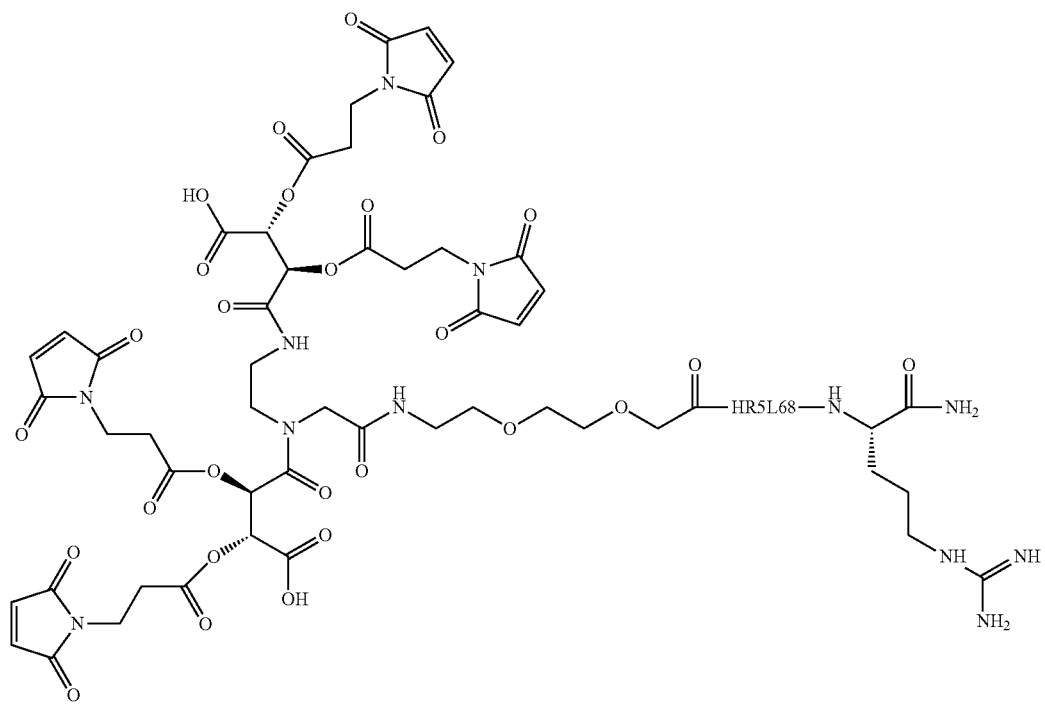

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide ole (MSNT) (4 eq). After complete dissolution, the mixture was mixed with the resin. The resulting mixture was shaken over night. The mixture was shaken for 24 h. The resin was washed and cleaved with 5% water in TFA. The compound was triturated with diethyl ether.

LC-MS: 1113 $(M+H)^{2+}$

Compound 20

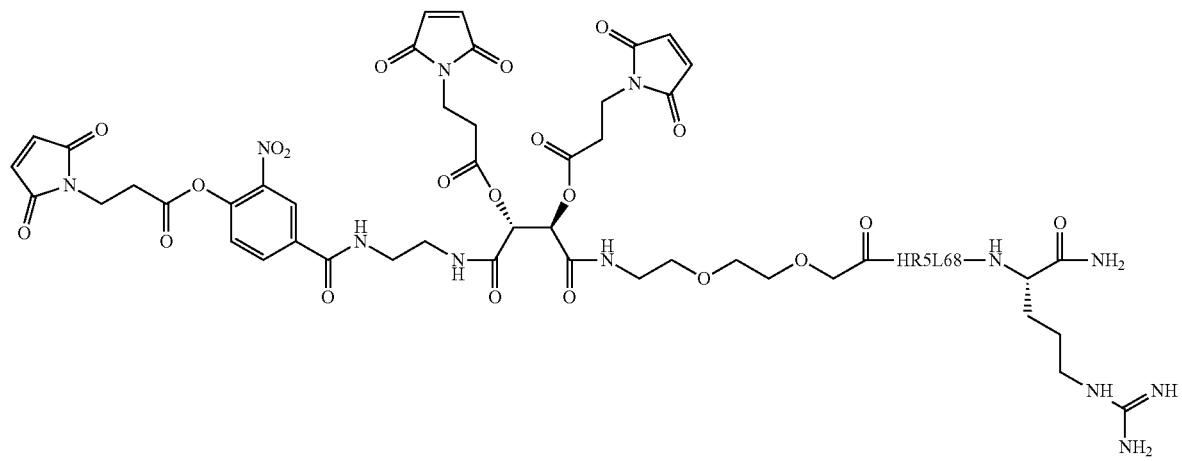

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

After removal of the N-terminal Fmoc protecting group and subsequent washing of the resin, a solution of (+)-diacetyl-L-tartaric anhydride (10 eq) in NMP was added to the resin. Bromophenol blue was used as monitoring reagent. The resin was washed with NMP after completion of the reaction.

A solution of ethylene diamine (25 eq) and PyBOP (5 eq) in NMP was added to the resin. The mixture was shaken for 3 hours. The resin was washed with NMP.

A solution of 4-hydroxy-3-nitrobenzoic acid (4 eq), HOAt (4 eq) and DIC (4 eq) in NMP was added to the resin. Bromophenol blue was used as monitoring reagent. The resin was washed with NMP. A solution of sat. sodium methoxide in methanol/THF (1:8) was added to the resin. The mixture was shaken for 1 hour. The resin was washed with NMP, 5% AcOH in NMP, NMP and DCM.

N-Maleoyl-β-alanine (4 eq) was suspended in DCM. N-methylimidazole (3 eq) was added. The mixture was shaken until the solution became clear. The solution was mixed with 1-(2-mesitylenesulfonyl)-3-nitro-1H-1,2,4-triazole (MSNT) (4 eq). After complete dissolution, the mixture was mixed with the resin. The resulting mixture was shaken over night. The mixture was shaken for 24 h. The resin was washed and cleaved with 5% water in TFA. The compound was triturated with diethyl ether.

LC-MS: 1025 (M+H)$^{2+}$

Compound 21

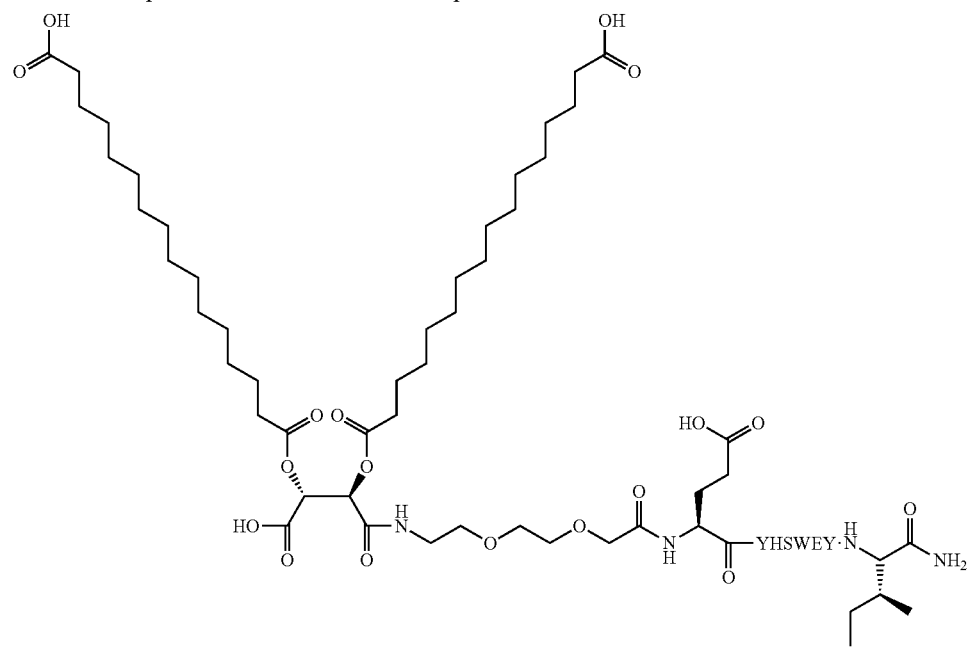

An Rink amide PS resin carrying the sequence Fmoc 8-amino-3,6-dioxaoctanoyl-Glu-Tyr-His-Ser-Trp-Glu-Tyr-Ile-NH$_2$ was placed in a fitted syringe. The resin was shaken in a mixture of piperidine and NMP (3:7) for approximately 1 minute. The syringe was drained. Piperidine in NMP (3:7) was added. The suspension was shaken for 30 minutes. The resin was washed with NMP. A solution of (+)-diacetyl-L-tartaric anhydride (10 eq.) in NMP was added to the resin. Bromophenol blue was used as monitoring reagent. The resin was washed with NMP shortly after completion of the reaction.

A solution of saturated sodium methoxide in methanol/THF (1:8) was added to the resin. The mixture was shaken for 1 h. The resin was washed with NMP, 5% AcOH in NMP, NMP and DCM. Hexanedioic acid (12 eq.) and DIC (12 eq.) were mixed in DCM. The resulting mixture was shaken. DMAP (6 eq.) was added. The mixture was mixed with the resin. The mixture was shaken over night. The resin was washed with DCM. The resin was treated with TFA containing 5% water for 2 h. Triturated with diethyl ether.

LC-MS: 970 (M+H)$^{2+}$

Compound 22 (Reference for One Step Modification)

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid (4 eq), 7-aza-1-hydroxybentriazole (4 eq), and N,N'-diisopropylcarbodiimide (4 eq) in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above.

The peptide was N-terminally acetylated by shaking the resin for 1 hour (h) in a solution of acetic anhydride (0.25 M) in NMP (10 ml). The resin was washed. The resin was treated with a mixture of hydrazine in NMP (3%, 8 ml) for 2×3 minutes. The resin was washed with NMP. The resin was shaken for 1 h in a mixture of phenyl chloroformate (10 eq)

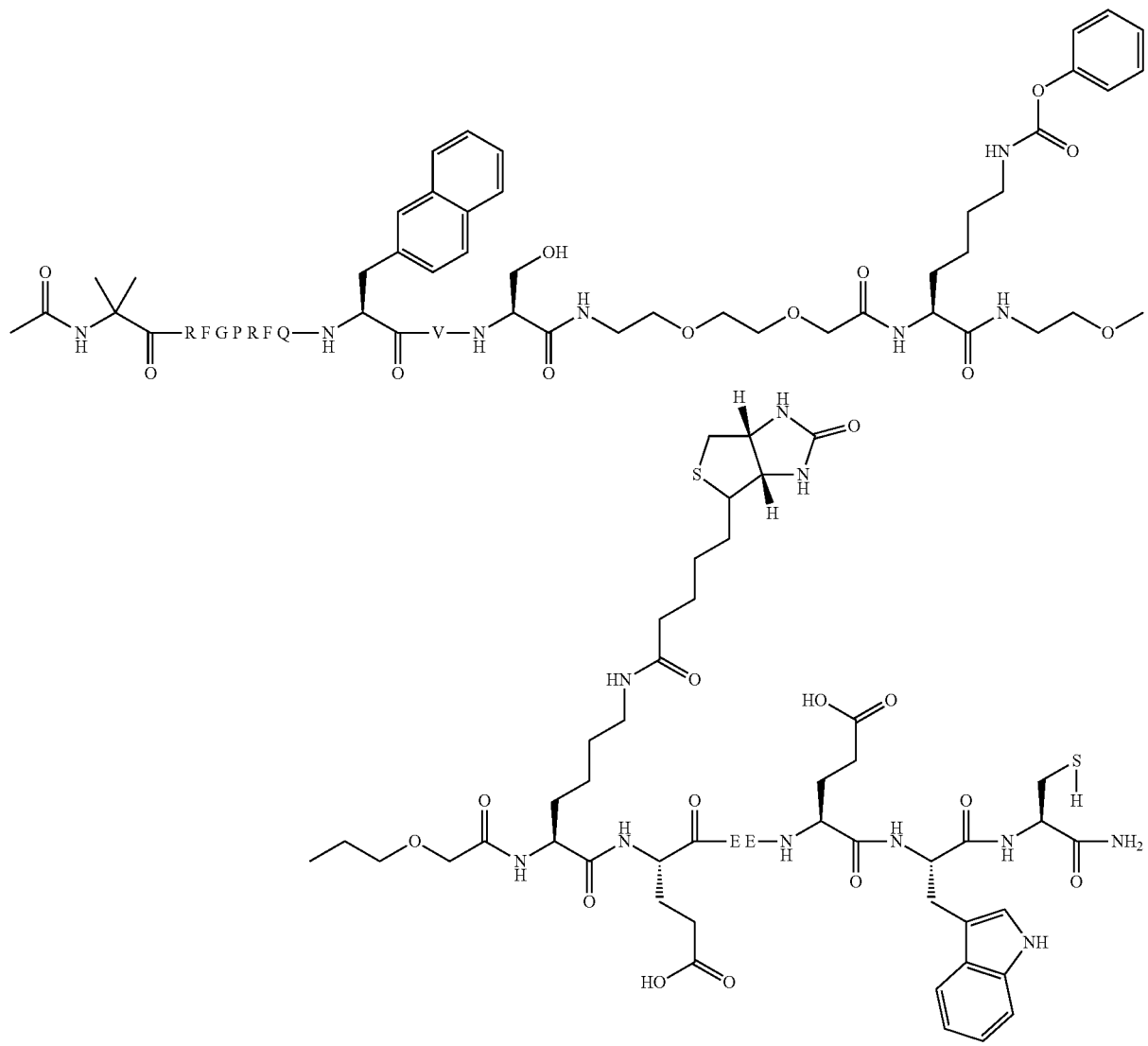

and DIPEA (15 eq) in NMP. The resin was washed with NMP and DCM. The peptide was cleaved from the resin by treating it with a solution of triethylsilane in TFA (5%, 2 ml) for 2 hours. The compound was triturated with diethyl ether. The crude compound was purified using reversed phase HPLC (25-45% MeCN in water with 0.1% trifluoroacetic acid, C8 column) The selected fractions were pooled and lyophilized.

LC-MS: 1558 (M+H)$^{2+}$

Label Compound 1

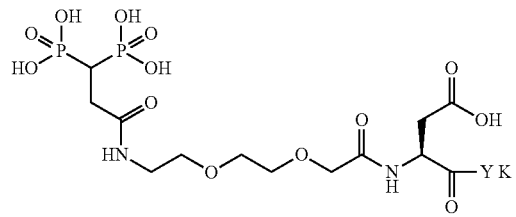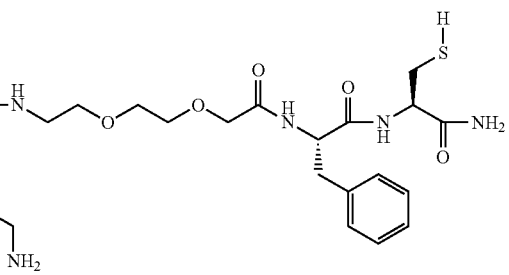

Rink amide linker aminomethyl polystyrene resin was placed in a syringe. The resin was shaken in a mixture of piperidine in N-methylpyrrolidone (NMP) (3:7, 10 ml) for 30 minutes. The resin was washed with NMP (5×10 ml). A pre-mixed solution of Fmoc-amino acid, 7-aza-1-hydroxybentriazole, and N,N'-diisopropylcarbodiimide in NMP was added to the resin. Bromophenol blue was used as monitoring reagent.

The suspension was shaken until the colour indicated complete acylation (pale green). The resin was washed with NMP (5×10 ml). Piperidine in NMP (3:7, 10 ml) was added. The resulting suspension was shaken for approximately 1 minute. The syringe was drained. Piperidine in NMP (3:7, 10 ml) was added. The suspension was shaken for 30 minutes.

Repetitive cycles of the protocol described above were used for synthesising the sequence listed above. The resin was washed. The 4-methylbenzyl-protected phosphonate was mixed with HOAt/HOBt and DIC in NMP (see attached sheet). The mixture was added to the resin.

The mixture was shaken over night. The peptide was cleaved from the resin by treatment with 5% mercaptoethanol, 5% triethylsilane, and 5% phenol in TFA (2 ml) for 2 hours. The crude peptide was triturated with diethyl ether.

LC-MS: 1768 (M+H)$^+$

Incubation of FVIII with Modifying Reagents

Incubation of B-Domain Deleted FVIII (N8) with Compound 22

B-domain deleted FVIII (0.244 mg/ml) was dissolved in the following buffer: 20 mM imidazole, 10 mM CaCl$_2$, 0.02% Tween 80, 150 mM NaCl, 1 M glycerol in water, pH 7.3. Compound 1 was dissolved partially in the same buffer that FVIII was dissolved in. Stock solutions of the carbamate were made with the dilution factors: 1 (for vial A), 10 (for vial B), 100 (for vial C), and 1000 (for vial D). FVIII solution (9 microliter) and Compound 23 solutions (5 microliter) were mixed. The samples were incubated at 25 degrees for 20 hours. The result was analysed by western blotting against Avidin-HRP.

The samples were loaded on a 7% tris-acetate gel (1.0 mm) The gel was exposed to 150 V for 60 minutes. The gel was electroblotted and the resulting blot was treated in a solution of: 3% milk powder in a buffer (wash buffer) consisting of 50 mM Tris, 150 mM NaCl, and Tween 20, pH 7.5 for 45 minutes. The blot was washed in the TBS buffer (no milk powder) for 5 minutes. The blot was incubated at room temperature for 2 h in: a 1:1000 mixture of avidin/HRP (cat#: P0347, from DakoCytomation, 1 g/l, 15 µM) and the buffer/milk powder mixture (blotto 3 buffer; 10 ml). The blot was washed with TBS buffer 4×5 minutes. The blot was treated with a West Pico luminescence mixture (5 ml) for 5 minutes. The chemiluminescence was measured immediately after.

The results are shown in FIG. 1. Each lane contains the following:

Lane 1: biotinylated marker cell signaling technologies, 2.5 microliter;
Lane 2: N8 (50 ng);
Lane 3: vial A (50 ng);
Lane 4: vial B (50 ng);
Lane 5: vial C (50 ng);
Lane 6: vial D (50 ng);
Lane 7: vial A (100 ng);
Lane 8: vial B (100 ng);
Lane 9: vial C (100 ng); and
Lane 10: vial D (100 ng);

FIG. 1 demonstrates that introduction of a biotin-substituent has taken place mainly in the heavy chain (HC).

Figure 2:
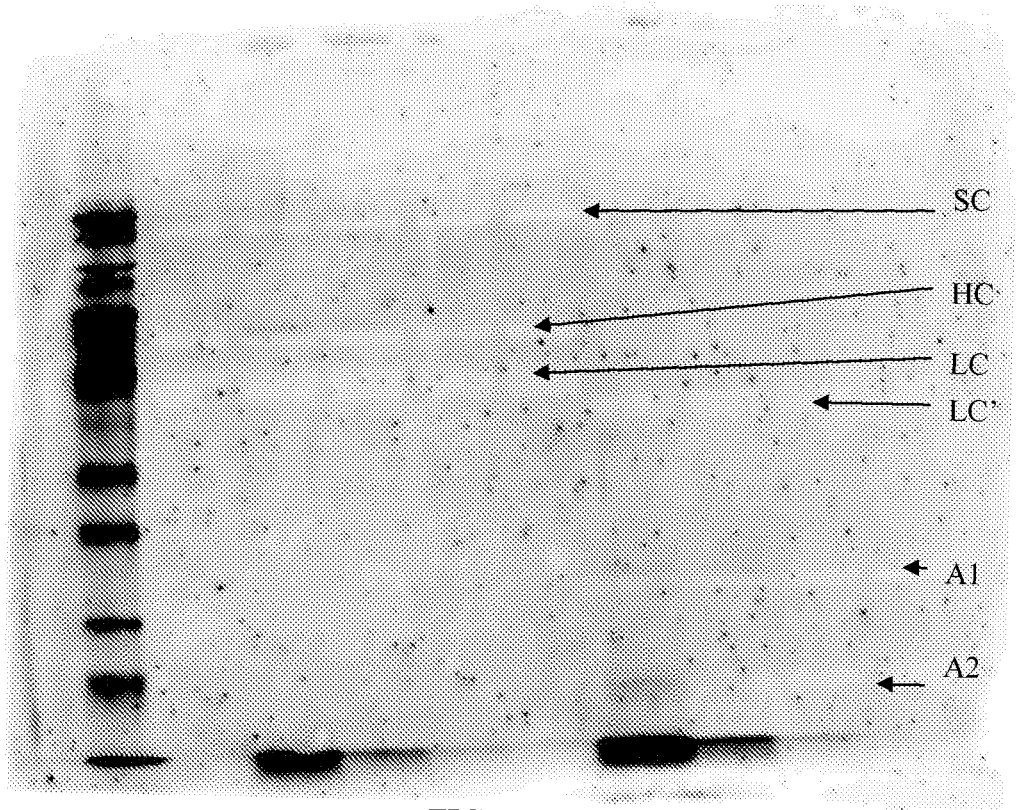
FIG. 2 is a Western blot obtained for the product formed from the reaction of Compound 22 with B domain deleted Factor VIII. Lanes: 1: Biotinylated marker cell signaling technologies, 2 microliter and seeblue 2 marker, 3 microliter; 2: BDD-FVIII (50 ng); 3-6: BDD-FVIII (300 ng protein pr. lane) incubated with solutions of compounds 22 in decreasing amounts (decrements of factor 10), 7-10: BDD-FVIII (300 ng protein pr. lane) incubated with solutions of compounds 22 in decreasing amounts (decrements of factor 10) and subsequently treated with thrombin. "HC" refers to "heavy chain", "LC" refers to "light chain", "SC" refers to single chain, and A1 and A2 refer to domains of Factor VIII. The Western blot demonstrates that biotin was introduced into the A2 domain of Factor VIII.

FIG. 2 is another Western Blot showing the following:

Lane 1: Biotinylated marker cell signaling technologies, 2 microliter and seeblue 2 marker, 3 microliter;
Lane 2: N8 batch 7 (300 ng);
Lane 3: vial A (300 ng);
Lane 4: vial B—compromised (300 ng);
Lane 5: vial C (300 ng);
Lane 6: vial D (300 ng);
Lane 7: vial A+Thrombin-pre-treatment (300 ng);
Lane 8: vial B+Thrombin-pre-treatment (300 ng);
Lane 9: vial C+Thrombin-pre-treatment (300 ng); and
Lane 10: vial D+Thrombin-pre-treatment (300 ng).

FIG. 2 demonstrates that introduction of a biotin-substituent has taken place in A2 domain mainly/only.

Incubation of B-Domain Deleted FVIII (N8) with Compound 17

B-domain deleted (BDD) FVIII was incubated at 25° C. for 20 hours with various concentrations of Compound 17 in the following buffer: 50 mM HEPES, 10 mM CaCl$_2$, 0.02% Tween 80, and 0.50 M NaCl in water, pH=7.5. Various concentrations of a solution of Label Compound 1 in the same buffer were added. The samples were incubated in vials for 4 or 18 hours. The amounts of Compound 17, Label Compound 1 and the incubation period are shown in Table 1.

Figure 3:
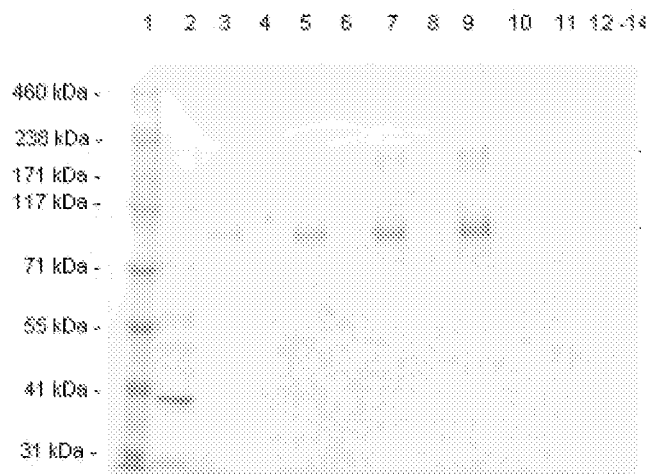
FIG. 3 is a Anti-FLAG Western blot (anti-FLAG M2 mAb, Sigma-Aldrich) obtained for the product formed from the reaction of Compound 17 with B domain deleted Factor VIII followed by subsequent incubation with label compound 1. Lanes 3-10 shows incubation o increasing amounts of site-directing peptide and subsequently a fixed amount of thiol reagent (150 eq) after 4 and 18 h. Lanes 11-14 shows products from incubation without site-directing peptide and the 2 latter lanes also without thiol reagent. After 18 h a significant amount of precipitate was formed which may explain the absence of signal in the lanes corresponding to 18 h of incubation. The observed signal corresponds to the B-domain deleted Factor VIII heavy chain.

The result were analysed by Western blotting against anti-FLAG M2 antibody (Sigma-Aldrich) and are shown in FIG. 3. Table 1 provides a key to FIG. 1. Lanes 1 and 2 were HiMark Pre-stained and Magic Mark XP Western Protein Stained respectively.

TABLE 1

| Lane | Compound 17 (equivalents) | Label Compound 1 (equivalents) | Incubation period (hours) |
|---|---|---|---|
| 3 | 25 | 150 | 4 |
| 4 | 25 | 150 | 18 |
| 5 | 50 | 150 | 4 |
| 6 | 50 | 150 | 18 |
| 7 | 100 | 150 | 4 |
| 8 | 100 | 150 | 18 |
| 9 | 150 | 150 | 4 |
| 10 | 150 | 150 | 18 |
| 11 | 0 | 150 | 4 |
| 12 | 0 | 150 | 18 |
| 13 | 0 | 0 | 4 |
| 14 | 0 | 0 | 18 |

Precipitation occurred in the vials left for 18 hours and may explain the absence of signal in these lanes. Increasing amounts of Compound 17 resulted in increased intensity of detected signal (see lanes 3, 5, 7 and 9). The signal is observed at a band corresponding to BDD-FVIII heavy chain only.

Incubation of B-Domain Deleted FVIII (N8) with Compound 17 Followed by PEGylation B-domain deleted (BDD) FVIII was incubated at 25° C. for 20 hours with various concentrations of Compound 17 in the following buffer: 50 mM HEPES, 10 mM $CaCl_2$, 0.02% Tween 80, and 0.50 M NaCl in water, pH=7.5.

Solution of polyethyleneoxy-thiol (20 kDa, Rapp polymer) in the same buffer were added. The samples were incubated for 4 or 18 hours. The concentrations of Compound 17 and polyethyleneoxy-thiol used and the incubation times are shown in Table 2.

Figure 4:
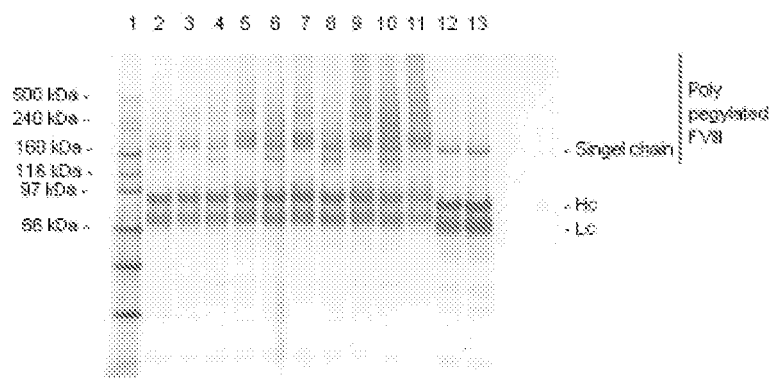
FIG. 4 is an SDS PAGE obtained for the product formed from the reaction of Compound 17 with B domain deleted Factor VIII. Subsequently, a PEG-thiol (20 kDa, Rapp Polymere, Germany) is added. After incubation for at room temp. for 4 h, the product mixture is analysed by SDS-PAGE. Lanes 2-11 shows incubation o increasing amounts of site-directing peptide and subsequently a fixed amount of thiol reagent (250 eq) after 4 and 18 h. Lanes 12-13 shows products from incubation without site-directing peptide and thiol reagent. "HC" refers to "heavy chain" and "LC" refers to "light chain". The Figure shows that increasing the amount of Compound 17 or increasing the incubation period resulted in an increase in the degree of PEGylation.

The resulting compounds were analysed by SDS-PAGE (7% Tris-acetate, 1.0 mm) The gel was exposed to 150 V for 60 minutes. The results are shown in FIG. 4, for which Table 2 provides a key. Lane 1 was a HiMark HMW Standard.

TABLE 2

| Lane | Compound 17 (equivalents) | Polyethyleneoxy-thiol (eqivalents) | Incubation period (hours) |
|---|---|---|---|
| 2 | 25 | 250 | 4 |
| 3 | 25 | 250 | 18 |
| 4 | 50 | 250 | 4 |
| 5 | 50 | 250 | 18 |
| 6 | 75 | 250 | 4 |
| 7 | 75 | 250 | 18 |
| 8 | 125 | 250 | 4 |
| 9 | 125 | 250 | 18 |
| 10 | 250 | 250 | 4 |
| 11 | 250 | 250 | 18 |
| 12 | 0 | 0 | 4 |
| 13 | 0 | 0 | 18 |

Incubation for 18 hours increased or with higher concentration of Compound 17 provided more extensive incorporation of PEG-substituents.

Incubation of B-Domain Deleted FVIII (N8) with Compound 19 Followed by PEGylation B-domain deleted (BDD) FVIII was incubated at 25° C. for 3 to 18 hours with various concentrations of Compound 19 in the following buffer: 50 mM HEPES, 10 mM $CaCl_2$, 0.02% Tween 80, and 0.50 M NaCl in water, pH=7.5.

A solution of polyethyleneoxy-thiol (20 kDa, Rapp polymer) in the same buffer was added. The samples were incubated for 4 or 18 hours. The concentrations of Compound 19 and polyethyleneoxy-thiol used and the incubation times are shown in Table 3.

Figure 5:
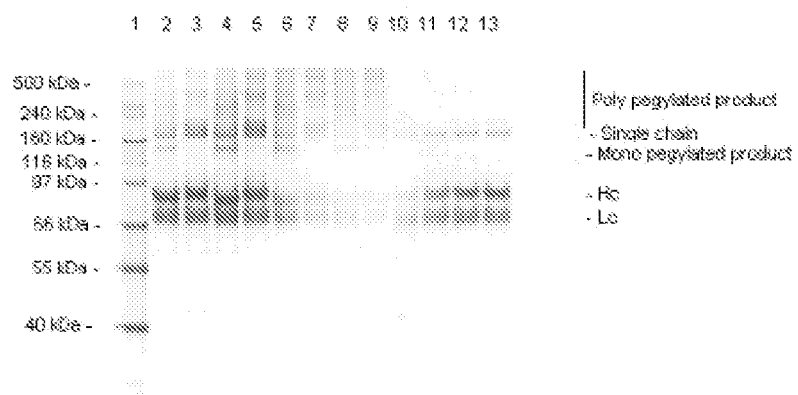
FIG. 5 is an SDS PAGE obtained for the product formed from PEGylation of the modified Factor VIII formed by reaction of Compound 19 with B domain deleted Factor VIII. Subsequently, a PEG-thiol (20 kDa, Rapp Polymere, Germany) is added. After incubation for at room temp. for 4 h, the product mixture is analysed by SDS-PAGE. Lanes 2-9 shows incubation o increasing amounts of site-directing peptide and subsequently a fixed amount of thiol reagent (150 eq). Lanes 10-13 shows products from incubation without site-directing peptide, the 2 latter lanes also without thiol reagent. "HC" refers to "heavy chain" and "LC" refers to "light chain". The Figure shows that increasing the amount of Compound 19 or increasing the incubation period resulted in an increase in the degree of PEGylation.

The resulting compounds were analysed by SDS-PAGE (7% Tris-acetate, 1.0 mm) The gel was exposed to 150 V for 60 minutes. The results are shown in FIG. 5, for which Table 3 provides a key. Lane 1 was a HiMark HMW Standard.

TABLE 3

| Lane | Compounds 19 (equivalents) | Polyethyleneoxy-thiol (equivalents) | Incubation period (hours) |
|---|---|---|---|
| 2 | 25 | 150 | 3 |
| 3 | 25 | 150 | 18 |
| 4 | 50 | 150 | 3 |
| 5 | 50 | 150 | 18 |
| 6 | 100 | 150 | 3 |
| 7 | 100 | 150 | 18 |
| 8 | 150 | 150 | 3 |
| 9 | 150 | 150 | 18 |
| 10 | 0 | 150 | 3 |
| 11 | 0 | 150 | 18 |
| 12 | 0 | 0 | 3 |
| 13 | 0 | 0 | 18 |

Incubation for 18 hours or with higher concentration of Compound 19 resulted in more extensive incorporation of PEG-substituents.

Incubation of B-Domain Deleted FVIII (N8) with Compound 19 Followed by PEGylation BDD-FVIII was incubated with Compound 19 and subsequently a 20 kDa PEG-thiol (from RAPP Polymere) at various concentrations. After treatment with thrombin, the resulting compounds were analysed by SDS-PAGE (7% Tris-acetate, 1.0 mm) The gel was exposed to 150 V for 60 minutes.

Figure 6:
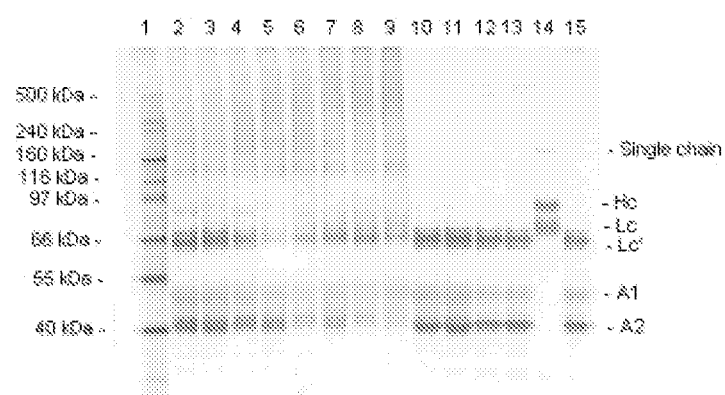
FIG. 6 is an SDS PAGE obtained for the product formed from PEGylation of the modified Factor VIII formed by reaction of Compound 19 with B domain deleted Factor VIII. Subsequently, a PEG-thiol (20 kDa, Rapp Polymere, Germany) is added. After incubation for at room temp. for 4 h, the samples are treated with thrombin and the product mixture is analysed by SDS-PAGE. Lanes 2-9 shows incubation o increasing amounts of site-directing peptide and subsequently a fixed amount of thiol reagent (150 eq) (with thrombin treatment). Lanes 10-13 shows products from incubation without site-directing peptide (with thrombin treatment). Lanes 14 and 15 shows FVIII without and with thrombin treatment, respectively. "HC" refers to "heavy chain", "LC" and "LC'" refer to "light chains", "SC" refers to "single chain", and A1 and A2 refer to domains of Factor VIII. Incorporation of a PEG substituent into the heavy chain/A2 domain was favoured.

The results of this are shown in FIG. 6, with Table 4 providing a key to the lanes. Lane 1 was a HiMark HMW Standard, Lane 14 was FVIII and Lane 15 was FVIII and thrombin.

TABLE 4

| Lane | Compound 19 (equivalents) | Polyethyleneoxy-thiol (equivalents) | Incubation period (hours) | Thrombin treated? |
|---|---|---|---|---|
| 2 | 25 | 150 | 3 | Yes |
| 3 | 25 | 150 | 18 | Yes |
| 4 | 50 | 150 | 3 | Yes |
| 5 | 50 | 150 | 18 | Yes |
| 6 | 75 | 150 | 3 | Yes |
| 7 | 75 | 150 | 18 | Yes |
| 8 | 100 | 150 | 3 | Yes |
| 9 | 100 | 150 | 18 | Yes |
| 10 | 0 | 150 | 3 | Yes |
| 11 | 0 | 150 | 18 | Yes |
| 12 | 0 | 0 | 3 | Yes |
| 13 | 0 | 0 | 18 | Yes |

Incubation for 18 hours or with higher concentration of resulted in more extensive incorporation of PEG-substituents.

Incorporation of the PEG substituent in heavy chain/A2 domain appeared favoured since the intensity of the bands from light chain and A1 did not seem significantly altered.

Use of the Methods According to the Invention for Modification of a Fab Fragment of an Antibody:

A derivative of peptide (homing peptide) known to bind to the Fab fragment of interest is prepared according to e.g., example 18 or 21. The horning peptide is incubated with said antibody/fragment in a buffer that can be considered suitable for acylation, e.g., HEPES or phosphate buffer, pH 7-9, containing appropriate additives such as Tween, sodium/calcium salts, at 5-40 degrees Celsius, The formed modified protein is purified using standard techniques such as ion exchange, gel permeation, and affinity-based. chromatography, hi case the incorporated substituent contains a label/tag (fluorophor, His tag etc.) it can be visualized using known analytical techniques.

The invention claimed is:

1. A method of selectively introducing a substituent (G) into a Factor VIII protein proximal to a binding site on the protein for a homing peptide (P), the method comprising:

(a) contacting the Factor VIII protein with a targeted reagent comprising a compound represented by formula (I):

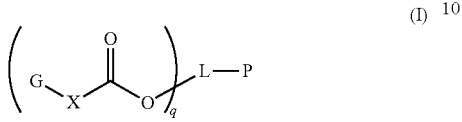

(I)

wherein:

P is a homing peptide comprising 5-15 amino acids,

L is a linker,

X is a direct bond or NH,

G is G1 or G2, wherein G1 comprises a functional group and G2 is a substituent that is capable of increasing the plasma half-life of the target protein, and q is an integer of from 1 to 9 wherein each G is the same or different if q is greater than 1; and (b) allowing a moiety on the protein proximal to the binding site to react with the targeted reagent, thereby to transfer the substituent G onto the protein via transfer of an acyl group from an ester group present in the targeted reagent to the protein.

2. The method according to claim 1, wherein the homing peptide does not contain any lysine residue that carries an unsubstituted epsilon-amino group, and wherein the target protein comprises a surface exposed lysine, and wherein the total mass of the targeted reagent does not exceed 3000 Da.

3. The method according to claim 1 wherein the homing peptide (P) is selected from the group consisting of any one of SEQ ID NOS: 1-44.

4. The method according to claim 1 wherein the linker L is a group of formula (II):

(II)

wherein:

$L_1$ represents a straight or branched $C_1$ to $C_{25}$ alkylene which is interrupted by one or more —O—, —NH—, —C(O)— or groups, said alkylene being unsubstituted or substituted by one or more halogen atoms;

$L_2$ represents a direct bond or a straight or branched $C_1$ to $C_{25}$ alkylene chain;

P' represents a direct bond or a peptide comprising 1 to 20 amino acids;

A represents a direct bond or a group of formula (III):

(III)

wherein Z represents a $C_6$ to $C_{10}$ arylene group which is unsubstituted or substituted with one or more nitro, $C_1$ to $C_6$ alkyl, $C_1$ to $C_6$ alkoxy, halogen or hydroxyl groups; a $C_1$ to $C_{1-10}$ alkylene group which is unsubstituted or substituted with one or more nitro, $C_1$ to $C_6$ alkoxy, halogen or hydroxyl groups; or a $C_3$ to $C_8$ cycloalkylene group which is unsubstituted or substituted with one or more nitro, $C_1$ to $C_6$ alkoxy, halogen or hydroxyl groups;

B represents a direct bond or a group of formula (IVa) or (IVb):

(IVa)

or (IVb)

m is an integer from 1 to 3; and n is an integer from 1 to 3.

5. The method of claim 1 wherein at least one of said substituents G is G1 substituent that comprises a functional group.

6. The method according to claim 5 wherein $G_1$ comprises an aldehyde, a ketone, an acetal, a hemiacetal, an azide, an alkyne, a pyridyl disulfide, an alkoxyamine or any derivative thereof.

7. The method of claim 5, further comprising:

(c) reacting the resulting protein carrying a substituent $G_1$ proximal to the binding site with a modifying reagent comprising a substituent R, thereby to provide a protein carrying said substituent R.

8. The method according to claim 7 wherein the substituent R is a substituent capable of increasing the plasma half-life of the protein.

9. The method of claim 7 wherein R comprises a bisphosphonate, a substituent that binds to platelets or endothelial cells, an antibody, a hydrophilic polymer, albumin or an albumin binder.

10. The method according to claim 9, wherein said hydrophilic polymer is polyethyleneglycol (PEG).

11. A protein which is substituted proximal to a binding site for a homing peptide on the protein and which is obtainable by the method of claim 1.

12. A pharmaceutical composition comprising a protein as defined in claim 11 and a pharmaceutically acceptable diluent or carrier.

* * * * *

```
                           SEQUENCE LISTING

<160> NUMBER OF SEQ ID NOS: 154

<210> SEQ ID NO 1
<211> LENGTH: 8
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Dip(L-diphenylalanine)

<400> SEQUENCE: 1

Arg Gln Xaa His Val Tyr Arg Gln
1               5

<210> SEQ ID NO 2
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (3)..(3)
<223> OTHER INFORMATION: L-Nal2 (L-2-Naphthylalanine)
<220> FEATURE:
<221> NAME/KEY: MISC_FEATURE
<222> LOCATION: (9)..(9)
<223> OTHER INFORMATION: L-Sty (Styrylalanine)

<400> SEQUENCE: 2

Xaa Arg Xaa His Gly Gly Tyr Gln Xaa Arg Val
1               5                   10

<210> SEQ ID NO 3
<211> LENGTH: 10
<212> TYPE: PRT
<213> ORGANISM: artificial
<220> FEATURE:
<223> OTHER INFORMATION: Synthetic homing peptide according to the
      present invention

<400> SEQUENCE: 3

Arg His Tyr Arg Val His Phe Gln Gly Arg
1               5                   10

<210> SEQ ID NO 4
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
```

```
<220> FEATURE:
<221> NAME/KEY: MISC_FEATURE
<222> LOCATION: (3)..(3)
<223> OTHER INFORMATION: L-Nal2 (L-2-Naphthylalanine)

<400> SEQUENCE: 4

Xaa His Xaa Arg Trp Gln Gln Gln Leu Asp Arg
1               5                   10

<210> SEQ ID NO 5
<211> LENGTH: 11
<212> TYPE: PRT
<213> ORGANISM: artificial
<220> FEATURE:
<223> OTHER INFORMATION: Synthetic homing peptide according to the
      invention
<220> FEATURE:
<221> NAME/KEY: MISC_FEATURE
<222> LOCATION: (3)..(3)
<223> OTHER INFORMATION: L-Nal2 (L-2-Naphthylalanine)
<220> FEATURE:
<221> NAME/KEY: MISC_FEATURE
<222> LOCATION: (6)..(6)
<223> OTHER INFORMATION: L-Tic (L-1,2,3,4-tetrahydroisoquinoline-3-
      carboxylic acid)

<400> SEQUENCE: 5

Val Gln Xaa Arg Gln Xaa Val Gln Tyr His Arg
1               5                   10

<210> SEQ ID NO 6
<211> LENGTH: 13
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (10)..(10)
<223> OTHER INFORMATION: L-Hph (L-homophenylalanine)
<220> FEATURE:
<221> NAME/KEY: MISC_FEATURE
<222> LOCATION: (11)..(11)
<223> OTHER INFORMATION: L-Tic (L-1,2,3,4-tetrahydroisoquinoline-3-
      carboxylic acid)

<400> SEQUENCE: 6

Val Arg Xaa Val Arg Gln Leu Arg Arg Xaa Xaa Ser His
1               5                   10

<210> SEQ ID NO 7
<211> LENGTH: 10
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Sty (Styrylalanine)
<220> FEATURE:
<221> NAME/KEY: MISC_FEATURE
<222> LOCATION: (5)..(5)
<223> OTHER INFORMATION: L-Nal2 (L-2-Naphthylalanine)

<400> SEQUENCE: 7
```

```
Val Arg Xaa Gln Xaa Gln Arg Leu Gln Ser
1               5                   10
```

<210> SEQ ID NO 8
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (5)..(5)
<223> OTHER INFORMATION: L-Dip (L-Diphenylalanine)
<220> FEATURE:
<221> NAME/KEY: MISC_FEATURE
<222> LOCATION: (9)..(9)
<223> OTHER INFORMATION: L-Dip (L-Diphenylalanine)

<400> SEQUENCE: 8

```
Val Arg Leu Arg Xaa Gln Gln Arg Xaa Gln His
1               5                   10
```

<210> SEQ ID NO 9
<211> LENGTH: 10
<212> TYPE: PRT
<213> ORGANISM: artificial
<220> FEATURE:
<223> OTHER INFORMATION: Synthetic homing peptide according to the
      invention
<220> FEATURE:
<221> NAME/KEY: MISC_FEATURE
<222> LOCATION: (3)..(3)
<223> OTHER INFORMATION: L-Sty (Styrylalanine)
<220> FEATURE:
<221> NAME/KEY: MISC_FEATURE
<222> LOCATION: (6)..(6)
<223> OTHER INFORMATION: Pya3 (L-3-pyridylalanine)
<220> FEATURE:
<221> NAME/KEY: MISC_FEATURE
<222> LOCATION: (7)..(7)
<223> OTHER INFORMATION: L-Hph (L-homophenylalanine)

<400> SEQUENCE: 9

```
Arg Arg Xaa Gly Gln Xaa Xaa Val Phe His
1               5                   10
```

<210> SEQ ID NO 10
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Sty (Styrylalanine)
<220> FEATURE:
<221> NAME/KEY: MISC_FEATURE
<222> LOCATION: (7)..(7)
<223> OTHER INFORMATION: L-Nal2 (L-2-Naphthylalanine)
<220> FEATURE:
<221> NAME/KEY: MISC_FEATURE
<222> LOCATION: (9)..(9)
<223> OTHER INFORMATION: L-Bip (L-Biphenylalanine)

<400> SEQUENCE: 10

```
His Arg Xaa Ser Gln Val Xaa Arg Xaa Asp Arg
1               5                   10
```

<210> SEQ ID NO 11

```
<211> LENGTH: 12
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (7)..(7)
<223> OTHER INFORMATION: L-Dip (L-Diphenylalanine)

<400> SEQUENCE: 11

Xaa Arg Phe Arg Gln Ser Xaa Arg Val Tyr Gln Val
1               5                   10

<210> SEQ ID NO 12
<211> LENGTH: 10
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Sty (Styrylalanine)
<220> FEATURE:
<221> NAME/KEY: MISC_FEATURE
<222> LOCATION: (4)..(4)
<223> OTHER INFORMATION: L-Hph (L-homophenylalanine)
<220> FEATURE:
<221> NAME/KEY: MISC_FEATURE
<222> LOCATION: (6)..(6)
<223> OTHER INFORMATION: L-Bip (L-Biphenylalanine)
<220> FEATURE:
<221> NAME/KEY: MISC_FEATURE
<222> LOCATION: (8)..(8)
<223> OTHER INFORMATION: L-Nal2 (L-2-Naphthylalanine)

<400> SEQUENCE: 12

Arg Gln Xaa Xaa Gly Xaa Arg Xaa His Gln
1               5                   10

<210> SEQ ID NO 13
<211> LENGTH: 10
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: L-Hph (L-homophenylalanine)
<220> FEATURE:
<221> NAME/KEY: MISC_FEATURE
<222> LOCATION: (3)..(3)
<223> OTHER INFORMATION: L-Nal2 (L-2-Naphthylalanine)
<220> FEATURE:
<221> NAME/KEY: MISC_FEATURE
<222> LOCATION: (5)..(5)
<223> OTHER INFORMATION: L-Bip (L-Biphenylalanine)

<400> SEQUENCE: 13

Xaa Arg Xaa Val Xaa Arg Asp Tyr Gln Gln
1               5                   10

<210> SEQ ID NO 14
<211> LENGTH: 12
```

```
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (7)..(7)
<223> OTHER INFORMATION: Pya3 (L-3-pyridylalanine)
<220> FEATURE:
<221> NAME/KEY: MISC_FEATURE
<222> LOCATION: (10)..(10)
<223> OTHER INFORMATION: L-Bip (L-Biphenylalanine)

<400> SEQUENCE: 14

Val Val Xaa Val Arg His Xaa His Arg Xaa Arg Gln
1               5                   10

<210> SEQ ID NO 15
<211> LENGTH: 12
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (6)..(6)
<223> OTHER INFORMATION: L-Hph (L-homophenylalanine)
<220> FEATURE:
<221> NAME/KEY: MISC_FEATURE
<222> LOCATION: (7)..(7)
<223> OTHER INFORMATION: Pya3 (L-3-pyridylalanine)
<220> FEATURE:
<221> NAME/KEY: MISC_FEATURE
<222> LOCATION: (10)..(10)
<223> OTHER INFORMATION: Pya3 (L-3-pyridylalanine)

<400> SEQUENCE: 15

Arg Gln Tyr Val Val Xaa Xaa Arg Arg Xaa Arg Gln
1               5                   10

<210> SEQ ID NO 16
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (6)..(6)
<223> OTHER INFORMATION: L-Dip (L-Diphenylalanine)
<220> FEATURE:
<221> NAME/KEY: MISC_FEATURE
<222> LOCATION: (7)..(7)
<223> OTHER INFORMATION: L-Hph (L-homophenylalanine)
<220> FEATURE:
<221> NAME/KEY: MISC_FEATURE
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: L-Nal2 (L-2-Naphthylalanine)

<400> SEQUENCE: 16
```

```
Arg Arg Xaa Val Arg Xaa Arg Val Xaa Val His
1               5                   10

<210> SEQ ID NO 17
<211> LENGTH: 8
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Pya3 (L-3-pyridylalanine)
<220> FEATURE:
<221> NAME/KEY: MISC_FEATURE
<222> LOCATION: (8)..(8)
<223> OTHER INFORMATION: L-Hph (L-homophenylalanine)

<400> SEQUENCE: 17

Xaa Arg Xaa Val Xaa Xaa Arg Xaa
1               5

<210> SEQ ID NO 18
<211> LENGTH: 10
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Dip (L-Diphenylalanine)
<220> FEATURE:
<221> NAME/KEY: MISC_FEATURE
<222> LOCATION: (5)..(5)
<223> OTHER INFORMATION: Pya3 (L-3-pyridylalanine)

<400> SEQUENCE: 18

His Gln Xaa Arg Xaa Val Ser Tyr Arg Arg
1               5                   10

<210> SEQ ID NO 19
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (2)..(2)
<223> OTHER INFORMATION: L-Hph (L-homophenylalanine)
<220> FEATURE:
<221> NAME/KEY: MISC_FEATURE
<222> LOCATION: (3)..(3)
```

```
<223> OTHER INFORMATION: Pya3 (L-3-pyridylalanine)
<220> FEATURE:
<221> NAME/KEY: MISC_FEATURE
<222> LOCATION: (5)..(5)
<223> OTHER INFORMATION: Pya3 (L-3-pyridylalanine)
<220> FEATURE:
<221> NAME/KEY: MISC_FEATURE
<222> LOCATION: (7)..(7)
<223> OTHER INFORMATION: L-Hph (L-homophenylalanine)
<220> FEATURE:
<221> NAME/KEY: MISC_FEATURE
<222> LOCATION: (9)..(9)
<223> OTHER INFORMATION: Pya3 (L-3-pyridylalanine)

<400> SEQUENCE: 19

Xaa Xaa Xaa Val Xaa Gln Xaa Arg Xaa His Arg
1               5                   10

<210> SEQ ID NO 20
<211> LENGTH: 7
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (2)..(2)
<223> OTHER INFORMATION: Pya3 (L-3-pyridylalanine)
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (5)..(5)
<223> OTHER INFORMATION: L-Bip (L-Biphenylalanine)

<400> SEQUENCE: 20

Arg Xaa Xaa Val Xaa His Arg
1               5

<210> SEQ ID NO 21
<211> LENGTH: 9
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (7)..(7)
<223> OTHER INFORMATION: Pya3 (L-3-pyridylalanine)
<220> FEATURE:
<221> NAME/KEY: MISC_FEATURE
<222> LOCATION: (8)..(8)
<223> OTHER INFORMATION: L-Hph (L-homophenylalanine)

<400> SEQUENCE: 21

Arg Ser Xaa Val Gly Arg Xaa Xaa Gln
1               5

<210> SEQ ID NO 22
<211> LENGTH: 7
<212> TYPE: PRT
<213> ORGANISM: artificial
<220> FEATURE:
<223> OTHER INFORMATION: Synthetic homing peptide according to the
      present invention
```

```
<220> FEATURE:
<221> NAME/KEY: MISC_FEATURE
<222> LOCATION: (3)..(3)
<223> OTHER INFORMATION: L-Bip (L-Biphenylalanine)
<220> FEATURE:
<221> NAME/KEY: MISC_FEATURE
<222> LOCATION: (5)..(5)
<223> OTHER INFORMATION: Pya3 (L-3-pyridylalanine)
<220> FEATURE:
<221> NAME/KEY: MISC_FEATURE
<222> LOCATION: (6)..(6)
<223> OTHER INFORMATION: L-Hph (L-homophenylalanine)

<400> SEQUENCE: 22

His Arg Xaa Leu Xaa Xaa Arg
1               5

<210> SEQ ID NO 23
<211> LENGTH: 13
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (7)..(7)
<223> OTHER INFORMATION: L-Sty (Styrylalanine)
<220> FEATURE:
<221> NAME/KEY: MISC_FEATURE
<222> LOCATION: (11)..(11)
<223> OTHER INFORMATION: Pya3 (L-3-pyridylalanine)
<220> FEATURE:
<221> NAME/KEY: MISC_FEATURE
<222> LOCATION: (12)..(12)
<223> OTHER INFORMATION: L-Hph (L-homophenylalanine)

<400> SEQUENCE: 23

Xaa Arg Leu His His Arg Xaa Val Arg Val Xaa Xaa Val
1               5                   10

<210> SEQ ID NO 24
<211> LENGTH: 13
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (7)..(7)
<223> OTHER INFORMATION: Pya3 (L-3-pyridylalanine)
<220> FEATURE:
<221> NAME/KEY: MISC_FEATURE
<222> LOCATION: (10)..(10)
<223> OTHER INFORMATION: L-Hph (L-homophenylalanine)
<220> FEATURE:
<221> NAME/KEY: MISC_FEATURE
<222> LOCATION: (11)..(11)
<223> OTHER INFORMATION: Pya3 (L-3-pyridylalanine)
<220> FEATURE:
<221> NAME/KEY: MISC_FEATURE
<222> LOCATION: (12)..(12)
<223> OTHER INFORMATION: L-Hph (L-homophenylalanine)

<400> SEQUENCE: 24

Asp Arg Leu Pro His Arg Xaa Ser Val Xaa Xaa Xaa Arg
1               5                   10
```

```
<210> SEQ ID NO 25
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (6)..(6)
<223> OTHER INFORMATION: Pya3 (L-3-pyridylalanine)
<220> FEATURE:
<221> NAME/KEY: MISC_FEATURE
<222> LOCATION: (7)..(7)
<223> OTHER INFORMATION: L-Hph (L-homophenylalanine)
<220> FEATURE:
<221> NAME/KEY: MISC_FEATURE
<222> LOCATION: (9)..(9)
<223> OTHER INFORMATION: L-Nal2 (L-2-Naphthylalanine)
<220> FEATURE:
<221> NAME/KEY: MISC_FEATURE
<222> LOCATION: (10)..(10)
<223> OTHER INFORMATION: Aib (2-aminoisobutyric acid)

<400> SEQUENCE: 25

Arg Gly Tyr Val His Xaa Xaa Arg Xaa Xaa His
1               5                   10

<210> SEQ ID NO 26
<211> LENGTH: 10
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Sty (Styrylalanine)
<220> FEATURE:
<221> NAME/KEY: MISC_FEATURE
<222> LOCATION: (6)..(6)
<223> OTHER INFORMATION: Pya3 (L-3-pyridylalanine)
<220> FEATURE:
<221> NAME/KEY: MISC_FEATURE
<222> LOCATION: (7)..(7)
<223> OTHER INFORMATION: L-Hph (L-homophenylalanine)

<400> SEQUENCE: 26

Arg Arg Xaa Gly Gln Xaa Xaa Val Phe His
1               5                   10

<210> SEQ ID NO 27
<211> LENGTH: 9
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (2)..(2)
<223> OTHER INFORMATION: Aib (2-aminoisobutyric acid)
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (4)..(4)
<223> OTHER INFORMATION: L-Hph (L-homophenylalanine)
<220> FEATURE:
<221> NAME/KEY: MISC_FEATURE
<222> LOCATION: (5)..(5)
<223> OTHER INFORMATION: Pya3 (L-3-pyridylalanine)
```

```
<400> SEQUENCE: 27

Arg Xaa Xaa Xaa Xaa Val Tyr Arg His
1               5

<210> SEQ ID NO 28
<211> LENGTH: 12
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (4)..(4)
<223> OTHER INFORMATION: L-Hph (L-homophenylalanine)
<220> FEATURE:
<221> NAME/KEY: MISC_FEATURE
<222> LOCATION: (10)..(10)
<223> OTHER INFORMATION: L-Bip (L-Biphenylalanine)

<400> SEQUENCE: 28

Asp His Xaa Xaa His Tyr Arg Arg Gly Xaa Gln Val
1               5                   10

<210> SEQ ID NO 29
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (10)..(10)
<223> OTHER INFORMATION: L-Hph (L-homophenylalanine)

<400> SEQUENCE: 29

Xaa His Tyr Arg Trp Val Arg Pro Leu Xaa Gly
1               5                   10

<210> SEQ ID NO 30
<211> LENGTH: 12
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (10)..(10)
<223> OTHER INFORMATION: L-Nal2 (L-2-Naphthylalanine)
<220> FEATURE:
<221> NAME/KEY: MISC_FEATURE
<222> LOCATION: (12)..(12)
<223> OTHER INFORMATION: L-Hph (L-homophenylalanine)

<400> SEQUENCE: 30

Val His Tyr Gly Arg Pro Leu Arg Gln Xaa Val Xaa
1               5                   10

<210> SEQ ID NO 31
<211> LENGTH: 11
```

```
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (3)..(3)
<223> OTHER INFORMATION: L-Nal2 (L-2-Naphthylalanine)
<220> FEATURE:
<221> NAME/KEY: MISC_FEATURE
<222> LOCATION: (11)..(11)
<223> OTHER INFORMATION: Aib (2-aminoisobutyric acid)

<400> SEQUENCE: 31

Xaa Val Xaa His Pro Tyr Arg Pro Leu Arg Xaa
1               5                   10

<210> SEQ ID NO 32
<211> LENGTH: 12
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (3)..(3)
<223> OTHER INFORMATION: L-Nal2 (L-2-Naphthylalanine)
<220> FEATURE:
<221> NAME/KEY: MISC_FEATURE
<222> LOCATION: (10)..(10)
<223> OTHER INFORMATION: L-Dip (L-Diphenylalanine)

<400> SEQUENCE: 32

Xaa Gln Xaa Arg Pro Tyr Ser Ser His Xaa His His
1               5                   10

<210> SEQ ID NO 33
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (7)..(7)
<223> OTHER INFORMATION: Pya3 (L-3-pyridylalanine)

<400> SEQUENCE: 33

Arg Gln Tyr Arg Pro His Xaa Val Trp His His
1               5                   10

<210> SEQ ID NO 34
<211> LENGTH: 9
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
```

```
<220> FEATURE:
<221> NAME/KEY: MISC_FEATURE
<222> LOCATION: (3)..(3)
<223> OTHER INFORMATION: L-Tic (L-1,2,3,4-tetrahydroisoquinoline-3-
      carboxylic acid)
<220> FEATURE:
<221> NAME/KEY: MISC_FEATURE
<222> LOCATION: (7)..(7)
<223> OTHER INFORMATION: L-Dip (L-Diphenylalanine)

<400> SEQUENCE: 34

Xaa Pro Xaa Arg Arg Phe Xaa His His
1               5

<210> SEQ ID NO 35
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (9)..(9)
<223> OTHER INFORMATION: Pya3 (L-3-pyridylalanine)
<220> FEATURE:
<221> NAME/KEY: MISC_FEATURE
<222> LOCATION: (11)..(11)
<223> OTHER INFORMATION: Aib (2-aminoisobutyric acid)

<400> SEQUENCE: 35

Arg Arg Trp Gln Arg His Trp Val Xaa Val Xaa
1               5                   10

<210> SEQ ID NO 36
<211> LENGTH: 9
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (2)..(2)
<223> OTHER INFORMATION: L-Hph (L-homophenylalanine)

<400> SEQUENCE: 36

Arg Xaa Tyr Leu Arg Arg Leu His Arg
1               5

<210> SEQ ID NO 37
<211> LENGTH: 9
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Bip (L-Biphenylalanine)
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: L-Nal2 (L-2-Naphthylalanine)

<400> SEQUENCE: 37

His Arg Xaa Ser Phe Arg Xaa Val His
```

```
<210> SEQ ID NO 38
<211> LENGTH: 12
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (3)..(3)
<223> OTHER INFORMATION: L-Bip (L-Biphenylalanine)
<220> FEATURE:
<221> NAME/KEY: MISC_FEATURE
<222> LOCATION: (6)..(6)
<223> OTHER INFORMATION: Pya3 (L-3-pyridylalanine)
<220> FEATURE:
<221> NAME/KEY: MISC_FEATURE
<222> LOCATION: (10)..(10)
<223> OTHER INFORMATION: Pya3 (L-3-pyridylalanine)
<220> FEATURE:
<221> NAME/KEY: MISC_FEATURE
<222> LOCATION: (12)..(12)
<223> OTHER INFORMATION: Aib (2-aminoisobutyric acid)

<400> SEQUENCE: 38

Gln Arg Xaa His Val Xaa Arg Val Ser Xaa Gly Xaa
1               5                   10

<210> SEQ ID NO 39
<211> LENGTH: 12
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (3)..(3)
<223> OTHER INFORMATION: L-Nal2 (L-2-Naphthylalanine)
<220> FEATURE:
<221> NAME/KEY: MISC_FEATURE
<222> LOCATION: (7)..(7)
<223> OTHER INFORMATION: L-Hph (L-homophenylalanine)

<400> SEQUENCE: 39

Xaa Arg Xaa Pro Arg Phe Xaa Arg Val Phe Pro Gly
1               5                   10

<210> SEQ ID NO 40
<211> LENGTH: 11
<212> TYPE: PRT
<213> ORGANISM: artificial
<220> FEATURE:
<223> OTHER INFORMATION: Synthetic homing peptide according to the
      present invention
<220> FEATURE:
<221> NAME/KEY: MISC_FEATURE
<222> LOCATION: (1)..(1)
<223> OTHER INFORMATION: Aib (2-aminoisobutyric acid)
<220> FEATURE:
<221> NAME/KEY: MISC_FEATURE
<222> LOCATION: (9)..(9)
<223> OTHER INFORMATION: L-Nal2 (L-2-Naphthylalanine)

<400> SEQUENCE: 40

Xaa Arg Phe Gly Pro Arg Phe Gln Xaa Val Ser
1               5                   10
```

<210> SEQ ID NO 41
<211> LENGTH: 11
<212> TYPE: PRT
<213> ORGANISM: artificial
<220> FEATURE:
<223> OTHER INFORMATION: Synthetic homing peptide according to the
     present invention
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (7)..(7)
<223> OTHER INFORMATION: L-Hph (L-homophenylalanine)
<220> FEATURE:
<221> NAME/KEY: MISC_FEATURE
<222> LOCATION: (9)..(9)
<223> OTHER INFORMATION: L-Nal2 (L-2-Naphthylalanine)

<400> SEQUENCE: 41

Arg Arg Xaa Gln Tyr Asp Xaa Arg Xaa Arg Arg
1               5                   10

<210> SEQ ID NO 42
<211> LENGTH: 7
<212> TYPE: PRT
<213> ORGANISM: artificial
<220> FEATURE:
<223> OTHER INFORMATION: Synthetic homing peptide according to the
     present invention
<220> FEATURE:
<221> NAME/KEY: MISC_FEATURE
<222> LOCATION: (2)..(2)
<223> OTHER INFORMATION: L-Hph (L-homophenylalanine)
<220> FEATURE:
<221> NAME/KEY: MISC_FEATURE
<222> LOCATION: (3)..(3)
<223> OTHER INFORMATION: Pya3 (L-3-pyridylalanine)
<220> FEATURE:
<221> NAME/KEY: MISC_FEATURE
<222> LOCATION: (5)..(5)
<223> OTHER INFORMATION: L-Bip (L-Biphenylalanine)

<400> SEQUENCE: 42

Arg Xaa Xaa Leu Xaa Arg His
1               5

<210> SEQ ID NO 43
<211> LENGTH: 8
<212> TYPE: PRT
<213> ORGANISM: artificial
<220> FEATURE:
<223> OTHER INFORMATION: Synthetic homing peptide according to the
     present invention

<400> SEQUENCE: 43

Ser Tyr Glu Trp Ser Gln Tyr Glu
1               5

<210> SEQ ID NO 44
<211> LENGTH: 11
<212> TYPE: PRT
<213> ORGANISM: artificial
<220> FEATURE:
<223> OTHER INFORMATION: Synthetic homing peptide according to the
     present invention
<220> FEATURE:
<221> NAME/KEY: MISC_FEATURE
<222> LOCATION: (3)..(3)
<223> OTHER INFORMATION: L-Nal2 (L-2-Naphthylalanine)

```
<220> FEATURE:
<221> NAME/KEY: MISC_FEATURE
<222> LOCATION: (11)..(11)
<223> OTHER INFORMATION: Aib (2-aminoisobutyric acid)

<400> SEQUENCE: 44

Ser Val Xaa Gln Phe Arg Pro Gly Phe Arg Xaa
1               5                   10

<210> SEQ ID NO 45
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 45

Gly Cys Val Ser Gly Cys Leu Cys
1               5

<210> SEQ ID NO 46
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 46

Cys Leu Cys Pro Pro Gly Met Val
1               5

<210> SEQ ID NO 47
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 47

Gly Met Val Arg His Glu Asn Arg
1               5

<210> SEQ ID NO 48
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 48

Glu Asn Arg Cys Val Ala Leu Glu
1               5

<210> SEQ ID NO 49
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 49

Ala Leu Glu Arg Cys Pro Cys Phe
1               5
```

<210> SEQ ID NO 50
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 50

Pro Cys Phe His Gln Gly Lys Glu
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic homing peptide according to the
      present invention

<400> SEQUENCE: 51

Gly Lys Glu Tyr Ala Pro Gly Glu
1               5

<210> SEQ ID NO 52
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 52

Pro Gly Glu Thr Val Lys Ile Gly
1               5

<210> SEQ ID NO 53
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 53

Lys Ile Gly Cys Asn Thr Cys Val
1               5

<210> SEQ ID NO 54
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 54

Thr Cys Val Cys Arg Asp Arg Lys
1               5

<210> SEQ ID NO 55
<211> LENGTH: 8
<212> TYPE: PRT
<213> ORGANISM: artificial
<220> FEATURE:
<223> OTHER INFORMATION: Synthetic homing peptide according to the
      present invention

```
<400> SEQUENCE: 55

Asp Arg Lys Trp Asn Cys Thr Asp
1               5

<210> SEQ ID NO 56
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 56

Val Met Ile Lys Cys Glu Glu Phe
1               5

<210> SEQ ID NO 57
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 57

Val Met Lys Ser Cys Glu Tyr Cys
1               5

<210> SEQ ID NO 58
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 58

Val Met Lys Ser Trp Glu Glu Phe
1               5

<210> SEQ ID NO 59
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 59

Glu Trp Ile Lys Trp Glu Tyr Cys
1               5

<210> SEQ ID NO 60
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 60

Glu Trp Lys Ser Glu Phe Glu Phe
1               5

<210> SEQ ID NO 61
<211> LENGTH: 8
```

<212> TYPE: PRT
<213> ORGANISM: artificial
<220> FEATURE:
<223> OTHER INFORMATION: Synthetic homing peptide according to the
      present invention

<400> SEQUENCE: 61

Glu Tyr Ile Lys Glu Phe Tyr Cys
1               5

<210> SEQ ID NO 62
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 62

Glu Tyr Lys Ser Cys Glu Glu Phe
1               5

<210> SEQ ID NO 63
<211> LENGTH: 10
<212> TYPE: PRT
<213> ORGANISM: artificial
<220> FEATURE:
<223> OTHER INFORMATION: Synthetic homing peptide according to the
      present invention

<400> SEQUENCE: 63

Leu Cys Pro Pro Gly Met Val Arg His Glu
1               5                   10

<210> SEQ ID NO 64
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 64

Cys Val Ser Gly Cys Leu Cys Pro
1               5

<210> SEQ ID NO 65
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 65

Leu Cys Asp Pro Gly Met Val Arg
1               5

<210> SEQ ID NO 66
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 66

Met Val Arg His Glu Asn Arg Cys

```
<210> SEQ ID NO 67
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 67

Asn Arg Cys Val Ala Leu Glu Arg
1               5

<210> SEQ ID NO 68
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 68

Leu Glu Arg Cys Pro Cys Phe His
1               5

<210> SEQ ID NO 69
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 69

Cys Phe His Gln Gly Lys Glu Tyr
1               5

<210> SEQ ID NO 70
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 70

Leu Glu Tyr Ala Pro Gly Glu Thr
1               5

<210> SEQ ID NO 71
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 71

Gly Glu Thr Val Lys Ile Gly Cys
1               5

<210> SEQ ID NO 72
<211> LENGTH: 8
<212> TYPE: PRT
<213> ORGANISM: artificial
<220> FEATURE:
<223> OTHER INFORMATION: Synthetic homing peptide according to the
```

-continued present invention

<400> SEQUENCE: 72

Ile Gly Cys Asn Thr Cys Val Cys
1               5

<210> SEQ ID NO 73
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 73

Cys Val Cys Arg Asp Arg Lys Trp
1               5

<210> SEQ ID NO 74
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 74

Arg Lys Trp Asn Cys Thr Asp His
1               5

<210> SEQ ID NO 75
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 75

Val Met Ile Lys Glu Phe Tyr Cys
1               5

<210> SEQ ID NO 76
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 76

Val Met Lys Ser Cys Glu Glu Phe
1               5

<210> SEQ ID NO 77
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 77

Glu Trp Ile Lys Cys Glu Tyr Cys
1               5

<210> SEQ ID NO 78

```
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 78

Glu Trp Ile Lys Trp Glu Glu Phe
1               5

<210> SEQ ID NO 79
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 79

Glu Trp Lys Ser Trp Glu Tyr Cys
1               5

<210> SEQ ID NO 80
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 80

Glu Tyr Ile Lys Glu Phe Glu Phe
1               5

<210> SEQ ID NO 81
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 81

Glu Tyr Lys Ser Glu Phe Tyr Cys
1               5

<210> SEQ ID NO 82
<211> LENGTH: 9
<212> TYPE: PRT
<213> ORGANISM: artificial
<220> FEATURE:
<223> OTHER INFORMATION: Synthetic homing peptide according to the
      present invention

<400> SEQUENCE: 82

Arg Cys Pro Cys Phe His Gln Gly Lys
1               5

<210> SEQ ID NO 83
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 83
```

```
Val Ser Gly Cys Leu Cys Pro Pro
1               5

<210> SEQ ID NO 84
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 84

Cys Pro Pro Gly Met Val Arg His
1               5

<210> SEQ ID NO 85
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 85

Val Arg His Glu Asn Arg Cys Val
1               5

<210> SEQ ID NO 86
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 86

Arg Cys Val Ala Leu Glu Arg Cys
1               5

<210> SEQ ID NO 87
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 87

Glu Arg Cys Pro Cys Phe His Gln
1               5

<210> SEQ ID NO 88
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 88

Phe His Gln Gly Lys Glu Tyr Ala
1               5

<210> SEQ ID NO 89
<211> LENGTH: 8
<212> TYPE: PRT
<213> ORGANISM: artificial
<220> FEATURE:
```

```
<223> OTHER INFORMATION: Synthetic homing peptide according to the
      present invention

<400> SEQUENCE: 89

Glu Tyr Ala Pro Gly Glu Thr Val
1               5

<210> SEQ ID NO 90
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 90

Gln Thr Val Lys Ile Gly Cys Asn
1               5

<210> SEQ ID NO 91
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 91

Gly Cys Asn Thr Cys Val Cys Arg
1               5

<210> SEQ ID NO 92
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 92

Val Cys Arg Asp Arg Lys Trp Asn
1               5

<210> SEQ ID NO 93
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 93

Lys Trp Asn Cys Thr Asp His Val
1               5

<210> SEQ ID NO 94
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 94

Val Met Ile Lys Glu Phe Glu Phe
1               5
```

```
<210> SEQ ID NO 95
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 95

Val Met Lys Ser Glu Phe Tyr Cys
1               5

<210> SEQ ID NO 96
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 96

Glu Trp Ile Lys Cys Glu Glu Phe
1               5

<210> SEQ ID NO 97
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 97

Glu Trp Lys Ser Cys Glu Tyr Cys
1               5

<210> SEQ ID NO 98
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 98

Glu Trp Lys Ser Trp Glu Glu Phe
1               5

<210> SEQ ID NO 99
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 99

Glu Tyr Ile Lys Trp Glu Tyr Cys
1               5

<210> SEQ ID NO 100
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 100
```

```
Glu Tyr Lys Ser Glu Phe Glu Phe
1               5
```

<210> SEQ ID NO 101
<211> LENGTH: 9
<212> TYPE: PRT
<213> ORGANISM: artificial
<220> FEATURE:
<223> OTHER INFORMATION: Synthetic homing peptide according to the
      present invention

<400> SEQUENCE: 101

```
Cys Phe His Gln Gly Lys Glu Tyr Ala
1               5
```

<210> SEQ ID NO 102
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 102

```
Ser Gly Cys Leu Cys Pro Pro Gly
1               5
```

<210> SEQ ID NO 103
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 103

```
Pro Pro Gly Met Val Arg His Glu
1               5
```

<210> SEQ ID NO 104
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 104

```
Arg His Glu Asn Arg Cys Val Ala
1               5
```

<210> SEQ ID NO 105
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 105

```
Cys Val Ala Leu Glu Arg Cys Pro
1               5
```

<210> SEQ ID NO 106
<211> LENGTH: 8
<212> TYPE: PRT
<213> ORGANISM: artificial

```
<220> FEATURE:
<223> OTHER INFORMATION: Synthetic homing peptide according to the
      present invention

<400> SEQUENCE: 106

Arg Cys Pro Cys Phe His Gln Gly
1               5

<210> SEQ ID NO 107
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 107

His Gln Gly Lys Glu Tyr Ala Pro
1               5

<210> SEQ ID NO 108
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 108

Tyr Ala Pro Gly Glu Thr Val Lys
1               5

<210> SEQ ID NO 109
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 109

Thr Val Lys Ile Gly Cys Asn Thr
1               5

<210> SEQ ID NO 110
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 110

Cys Asn Thr Cys Val Cys Arg Asp
1               5

<210> SEQ ID NO 111
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 111

Cys Arg Asp Arg Lys Trp Asn Cys
1               5
```

```
<210> SEQ ID NO 112
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 112

Trp Asn Cys Thr Asp His Val Cys
1               5

<210> SEQ ID NO 113
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 113

Val Met Ile Lys Trp Glu Tyr Cys
1               5

<210> SEQ ID NO 114
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 114

Val Met Lys Ser Glu Phe Glu Phe
1               5

<210> SEQ ID NO 115
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 115

Glu Trp Ile Lys Glu Phe Tyr Cys
1               5

<210> SEQ ID NO 116
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 116

Glu Trp Lys Ser Cys Glu Glu Phe
1               5

<210> SEQ ID NO 117
<211> LENGTH: 8
<212> TYPE: PRT
<213> ORGANISM: artificial
<220> FEATURE:
<223> OTHER INFORMATION: Synthetic homing peptide according to the
      present invention
```

```
<400> SEQUENCE: 117

Glu Tyr Ile Lys Cys Glu Tyr Cys
1               5

<210> SEQ ID NO 118
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 118

Glu Tyr Ile Lys Trp Glu Glu Phe
1               5

<210> SEQ ID NO 119
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 119

Glu Tyr Lys Ser Trp Glu Tyr Cys
1               5

<210> SEQ ID NO 120
<211> LENGTH: 12
<212> TYPE: PRT
<213> ORGANISM: artificial
<220> FEATURE:
<223> OTHER INFORMATION: Synthetic homing peptide according to the
      present invention

<400> SEQUENCE: 120

Arg Asp Arg Lys Trp Asn Cys Thr Asp His Val Cys
1               5                   10

<210> SEQ ID NO 121
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 121

Gly Cys Leu Cys Pro Pro Cys Met
1               5

<210> SEQ ID NO 122
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 122

Pro Gly Met Val Arg His Glu Asn
1               5

<210> SEQ ID NO 123
<211> LENGTH: 8
<212> TYPE: PRT
```

```
<213> ORGANISM: artificial
<220> FEATURE:
<223> OTHER INFORMATION: Synthetic homing peptide according to the
      present invention

<400> SEQUENCE: 123

His Glu Asn Arg Cys Val Ala Leu
1               5

<210> SEQ ID NO 124
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 124

Val Ala Leu Glu Arg Cys Pro Cys
1               5

<210> SEQ ID NO 125
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 125

Cys Pro Cys Phe His Gln Gly Lys
1               5

<210> SEQ ID NO 126
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 126

Cys Pro Cys Phe His Gln Gly Lys
1               5

<210> SEQ ID NO 127
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 127

Ala Pro Gly Glu Thr Val Lys Ile
1               5

<210> SEQ ID NO 128
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 128

Val Lys Ile Gly Cys Asn Thr Cys
1               5
```

<210> SEQ ID NO 129
<211> LENGTH: 8
<212> TYPE: PRT
<213> ORGANISM: artificial
<220> FEATURE:
<223> OTHER INFORMATION: Synthetic homing peptide according to the
present invention

<400> SEQUENCE: 129

Asn Thr Cys Val Cys Arg Asp Arg
1               5

<210> SEQ ID NO 130
<211> LENGTH: 8
<212> TYPE: PRT
<213> ORGANISM: artificial
<220> FEATURE:
<223> OTHER INFORMATION: Synthetic homing peptide according to the
present invention

<400> SEQUENCE: 130

Arg Asp Arg Lys Trp Asn Cys Thr
1               5

<210> SEQ ID NO 131
<211> LENGTH: 8
<212> TYPE: PRT
<213> ORGANISM: artificial
<220> FEATURE:
<223> OTHER INFORMATION: Synthetic homing peptide according to the
present invention

<400> SEQUENCE: 131

Val Met Ile Lys Cys Glu Tyr Cys
1               5

<210> SEQ ID NO 132
<211> LENGTH: 8
<212> TYPE: PRT
<213> ORGANISM: artificial
<220> FEATURE:
<223> OTHER INFORMATION: Synthetic homing peptide according to the
present invention

<400> SEQUENCE: 132

Val Met Ile Lys Trp Glu Glu Phe
1               5

<210> SEQ ID NO 133
<211> LENGTH: 8
<212> TYPE: PRT
<213> ORGANISM: artificial
<220> FEATURE:
<223> OTHER INFORMATION: Synthetic homing peptide according to the
present invention

<400> SEQUENCE: 133

Val Met Lys Ser Trp Glu Tyr Cys
1               5

<210> SEQ ID NO 134
<211> LENGTH: 8
<212> TYPE: PRT
<213> ORGANISM: artificial
<220> FEATURE:
<223> OTHER INFORMATION: Synthetic homing peptide according to the
present invention

<400> SEQUENCE: 134

Glu Trp Ile Lys Glu Phe Glu Phe
1               5

<210> SEQ ID NO 135
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 135

Glu Trp Lys Ser Glu Phe Tyr Cys
1               5

<210> SEQ ID NO 136
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 136

Glu Tyr Ile Lys Cys Glu Glu Phe
1               5

<210> SEQ ID NO 137
<211> LENGTH: 7
<212> TYPE: PRT
<213> ORGANISM: artificial
<220> FEATURE:
<223> OTHER INFORMATION: Synthetic homing peptide according to the
      present invention

<400> SEQUENCE: 137

Glu Tyr Lys Cys Glu Tyr Cys
1               5

<210> SEQ ID NO 138
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 138

Glu Tyr Lys Ser Trp Glu Glu Phe
1               5

<210> SEQ ID NO 139
<211> LENGTH: 8
<212> TYPE: PRT
<213> ORGANISM: artificial
<220> FEATURE:
<223> OTHER INFORMATION: Synthetic homing peptide according to the
      present invention

<400> SEQUENCE: 139

Glu Tyr His Ser Trp Glu Tyr Cys
1               5

<210> SEQ ID NO 140
<211> LENGTH: 18

```
<212> TYPE: PRT
<213> ORGANISM: artificial
<220> FEATURE:
<223> OTHER INFORMATION: Synthetic homing peptide according to the
      present invention

<400> SEQUENCE: 140

Ala Leu Cys Asp Asp Pro Arg Val Asp Arg Trp Tyr Cys Gln Phe Val
1               5                   10                  15

Glu Gly

<210> SEQ ID NO 141
<211> LENGTH: 15
<212> TYPE: PRT
<213> ORGANISM: artificial
<220> FEATURE:
<223> OTHER INFORMATION: Synthetic homing peptide according to the
      present invention

<400> SEQUENCE: 141

Glu Glu Trp Glu Val Leu Cys Trp Thr Trp Glu Thr Cys Glu Arg
1               5                   10                  15

<210> SEQ ID NO 142
<211> LENGTH: 20
<212> TYPE: PRT
<213> ORGANISM: artificial
<220> FEATURE:
<223> OTHER INFORMATION: Synthetic homing peptide according to the
      present invention

<400> SEQUENCE: 142

Glu Ala Ala Leu Cys Asp Asp Pro Arg Leu Asp Arg Trp Tyr Cys Ile
1               5                   10                  15

Phe Ala Gly Glu
            20

<210> SEQ ID NO 143
<211> LENGTH: 16
<212> TYPE: PRT
<213> ORGANISM: artificial
<220> FEATURE:
<223> OTHER INFORMATION: Synthetic homing peptide according to the
      present invention

<400> SEQUENCE: 143

Glu Trp Glu Val Leu Cys Trp Thr Trp Glu Thr Cys Glu Arg Gly Glu
1               5                   10                  15

<210> SEQ ID NO 144
<211> LENGTH: 18
<212> TYPE: PRT
<213> ORGANISM: artificial
<220> FEATURE:
<223> OTHER INFORMATION: Synthetic homing peptide according to the
      present invention

<400> SEQUENCE: 144

Glu Glu Trp Glu Val Leu Cys Trp Thr Trp Glu Thr Cys Glu Arg Gly
1               5                   10                  15

Glu Gly

<210> SEQ ID NO 145
<211> LENGTH: 20
<212> TYPE: PRT
<213> ORGANISM: artificial
```

```
<220> FEATURE:
<223> OTHER INFORMATION: Synthetic homing peptide according to the
      present invention

<400> SEQUENCE: 145

Met Glu Glu Trp Glu Val Leu Cys Trp Thr Trp Glu Thr Cys Glu Arg
1               5                   10                  15

Gly Glu Gly Gln
            20

<210> SEQ ID NO 146
<211> LENGTH: 12
<212> TYPE: PRT
<213> ORGANISM: artificial
<220> FEATURE:
<223> OTHER INFORMATION: Synthetic homing peptide according to the
      present invention

<400> SEQUENCE: 146

Glu Val Leu Cys Trp Thr Trp Glu Thr Cys Glu Arg
1               5                   10

<210> SEQ ID NO 147
<211> LENGTH: 10
<212> TYPE: PRT
<213> ORGANISM: artificial
<220> FEATURE:
<223> OTHER INFORMATION: Synthetic homing peptide according to the
      present invention

<400> SEQUENCE: 147

Leu Cys Trp Thr Trp Glu Thr Cys Glu Arg
1               5                   10

<210> SEQ ID NO 148
<211> LENGTH: 13
<212> TYPE: PRT
<213> ORGANISM: artificial
<220> FEATURE:
<223> OTHER INFORMATION: Synthetic homing peptide according to the
      present invention

<400> SEQUENCE: 148

Cys Trp Thr Trp Glu Thr Cys Glu Arg Gly Glu Gly Gln
1               5                   10

<210> SEQ ID NO 149
<211> LENGTH: 12
<212> TYPE: PRT
<213> ORGANISM: artificial
<220> FEATURE:
<223> OTHER INFORMATION: Synthetic homing peptide according to the
      present invention

<400> SEQUENCE: 149

Trp Glu Val Leu Cys Trp Thr Trp Glu Thr Cys Glu
1               5                   10

<210> SEQ ID NO 150
<211> LENGTH: 11
<212> TYPE: PRT
<213> ORGANISM: artificial
<220> FEATURE:
<223> OTHER INFORMATION: Synthetic homing peptide according to the
      present invention

<400> SEQUENCE: 150
```

```
Trp Glu Val Leu Cys Trp Thr Trp Glu Thr Cys
1               5                   10

<210> SEQ ID NO 151
<211> LENGTH: 20
<212> TYPE: PRT
<213> ORGANISM: artificial
<220> FEATURE:
<223> OTHER INFORMATION: Synthetic homing peptide according to the
      present invention

<400> SEQUENCE: 151

Ser Ala Glu Trp Glu Val Leu Cys Trp Thr Trp Glu Gly Cys Gly Ser
1               5                   10                  15

Val Gly Leu Val
            20

<210> SEQ ID NO 152
<211> LENGTH: 20
<212> TYPE: PRT
<213> ORGANISM: artificial
<220> FEATURE:
<223> OTHER INFORMATION: Synthetic homing peptide according to the
      present invention

<400> SEQUENCE: 152

Ser Glu Glu Trp Glu Val Leu Cys Trp Thr Trp Glu Asp Cys Arg Leu
1               5                   10                  15

Glu Gly Leu Glu
            20

<210> SEQ ID NO 153
<211> LENGTH: 20
<212> TYPE: PRT
<213> ORGANISM: artificial
<220> FEATURE:
<223> OTHER INFORMATION: Synthetic homing peptide according to the
      present invention

<400> SEQUENCE: 153

Glu Gly Thr Leu Cys Asp Asp Pro Arg Ile Asp Arg Trp Tyr Cys Met
1               5                   10                  15

Phe Ser Gly Val
            20

<210> SEQ ID NO 154
<211> LENGTH: 13
<212> TYPE: PRT
<213> ORGANISM: artificial
<220> FEATURE:
<223> OTHER INFORMATION: Synthetic homing peptide according to the
      present invention

<400> SEQUENCE: 154

Trp Glu Val Leu Cys Trp Thr Trp Glu Thr Cys Glu Arg
1               5                   10
```